(12) United States Patent
Bloch et al.

(10) Patent No.: US 7,087,717 B2
(45) Date of Patent: Aug. 8, 2006

(54) SP110, A POLYPEPTIDE COMPONENT OF THE NUCLEAR BODY

(75) Inventors: Donald B. Bloch, Newton, MA (US); Kenneth D. Bloch, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/333,227

(22) PCT Filed: Jul. 24, 2001

(86) PCT No.: PCT/US01/23248

§ 371 (c)(1), (2), (4) Date: Apr. 14, 2003

(87) PCT Pub. No.: WO02/08383

PCT Pub. Date: Jan. 31, 2002

(65) Prior Publication Data

US 2003/0216548 A1 Nov. 20, 2003

Related U.S. Application Data

(60) Provisional application No. 60/220,305, filed on Jul. 24, 2000.

(51) Int. Cl.
*A61K 38/00* (2006.01)
*A61K 38/16* (2006.01)
*C07K 14/00* (2006.01)
*C07K 16/00* (2006.01)
*C07K 17/00* (2006.01)
*C07K 5/00* (2006.01)
*C07K 7/00* (2006.01)

(52) U.S. Cl. .................. 530/350; 530/300; 530/324; 530/344; 530/358; 424/185.1

(58) Field of Classification Search ................ 530/300, 530/324, 350
See application file for complete search history.

(56) References Cited

U.S. PATENT DOCUMENTS

| 5,652,122 | A | 7/1997 | Frankel et al. | ............ | 435/69.7 |
| 6,183,988 | B1 | 2/2001 | Bloch et al. | ............ | 435/69.1 |
| 6,783,961 | B1 * | 8/2004 | Edwards et al. | ........... | 435/91.1 |
| 2003/0216548 | A1 * | 11/2003 | Bloch et al. | ............ | 530/350 |
| 2004/0171012 | A1 * | 9/2004 | Yue et al. | ............ | 435/6 |
| 2004/0171823 | A1 * | 9/2004 | Nadler et al. | ............ | 536/23.2 |

FOREIGN PATENT DOCUMENTS

| WO | WO 98/14569 | 4/1998 |
| WO | WO 02/08383 | 1/2002 |

OTHER PUBLICATIONS

Negorev et al, J. Cell Science, 2000, 114:59-68.*
Rasheed et al, Experimental Cell Research, 2002, 277:152-160.*
Zimber et al, Cellular Signalling, 2004, 16:1085-1104.*
Strausberg et al, PNAS, USA, 2002, 99/26:16899-16903.*
Wiesmeijer et al, J. Structural Biology, 2002, 140/1-3:180-188 abstract only.*
Muller et al, J. Virology, 1999, 73/6:5137-5143 abstract only.*
Sternsdorf et al, JBC, 1999, 274/18:12555-12566.*
Regad et al, Oncogene, 2001, 20:7274-7486.*
Seeler et al, current Opinion in Genetics and Development, 1999, 9:362-367.*
Puvion-Dutilleul et al, Experimental Cell Research, 1995, 221:448-461.*
Liettig et al, J. Hepatology, 1998, 28:824-828.*
International Search Report for corresponding international application no. PCT/US01/23248 (Jul. 24, 2003).
Bloch et al., Database GenBank, Accession No. AF280095, Submitted Jun. 20, 2000.
Bloch et al., "Sp110 Localizes to the PML-Sp100 Nuclear Body and May Function as a Nuclear Hormone Receptor Transcriptional Coactivator," *Mol. Cell. Biol.* 20:6138-6146, 2000.
Neto et al., "Shotgun sequencing of the human transcriptome with ORF expressed sequence tags," *PNAS* 97:3491-3496, 2000.
The Sanger Centre et al., "Progress Toward a Complete Human Genome Sequence," *Genome Res.* 8:1097-1108, 1998.
Seeler et al., "Common Properties of Nuclear Body Protein SP100 and TIF1 α Chromatin Factor: Role of SUMO Modification," *Mol. Cell. Biol.* 21:3314-3324, 2001.

(Continued)

*Primary Examiner*—N. M. Minnifield
(74) *Attorney, Agent, or Firm*—Fish & Richardson P.C.

(57) ABSTRACT

Cloning and characterization of a full length cDNA encoding Sp110 (speckled 110), a novel 110 kDa polypeptide, is disclosed. It is disclosed that Sp110 is a component of the nuclear body, is expressed in leukocytes, and is also expressed in other types of cells, including endothelial cells, smooth muscle cells, liver cells and heart cells, after contact with certain cytokines. The disclosure also includes the following: Sp140 recruits Sp110 to the nuclear body, Sp110 functions as an activator of gene transcription, and Sp110 serves as a nuclear hormone receptor co-activator. Sp110 DNAs, polypeptides, antibodies are disclosed. Also disclosed are Sp110-related screening methods and clinical diagnostic methods.

16 Claims, 17 Drawing Sheets

OTHER PUBLICATIONS

Aasland et al., "The PHD finger: implications for chromatin-mediated transcriptional regulation," Trends Biochem. Sci. 20:56-59 (1995).

Altschul et al., "Gapped BLAST and PSI-BLAST: a new generation of protein database search programs," Nucleic Acids Research 25: 3389-3402 (1997).

Ascoli et al., "Identification of a novel nuclear domain.," J. Cell Biol. 112: 785-795 (1991).

Bloch et al., "Serum antibodies to heat shock protein 70 in sensorineural hearing loss," Archives of Otolaryngology-Head and Neck Surgery 121:1167-1171 (1995).

Bloch et al., "Identification and characterization of a leukocyte-specific component of the nuclear body," J. Biol. Chem. 271: 29198-29204 (1996).

Bloch et al., "Structural and functional heterogeneity of nuclear bodies," Mol. Cell. Biol. 19:4423-4430 (1999).

Bonfanti et al., "p21WAF1-derived peptides linked to an internalization peptide inhibit human cancer cell growth," Cancer Res. 57:1442-1446 (1997).

Brownell et al., "Tetrahymena Histone Acetyltransferase A: A Homolog to Yeast Gcn5p Linking Histone Acetylation to Gene Activation," Cell 84: 843-851 (1996).

Dent et al., "LYSP100-associated nuclear domains (LANDs): description of a new class of subnuclear structures and their relationship to PML nuclear bodies," Blood 88:1423-1436 (1996).

Dikstein et al., "$TAF_{II}250$ Is a Bipartite Protein Kinase That Phosphorylates the Basal Transcription Factor RAP74," Cell 84:781-790 (1996).

Doucas et al., "Modulation of CREB binding protein function by the promyelocytic (PML) oncoprotein suggests a role for nuclear bodies in hormone signaling.," Proc. Natl. Acad. Sci. USA 96:2627-2632 (1999).

Fraser et al., "The putative cofactor TIF1alpha is a protein kinase that is hyperphosphorylated upon interaction with liganded nuclear receptors.," J. Biol. Chem. 273:16199-16204 (1998).

Gibson et al., "The APECED polyglandular autoimmune syndrome protein, AIRE-1, contains the SAND domain and is probably a transcription factor," Trends Biochem. Sci. 23:242-244 (1998).

Giles et al., "Conjunction dysfunction: CBP/p300 in human disease," Trends Genet 14:178-183 (1998).

Gross et al., "DEAF-1, a novel protein that binds an essential region in a Deformed response element," EMBO J. 15:1961-1970 (1996).

Gulick et al., "The peroxisome proliferator-activated receptor regulates mitochondrial fatty acid oxidative enzyme gene expression," Proc. Natl. Acad. Sci., USA 91:11012-11016 (1994).

Haynes et al., "The bromodomain: a conserved sequence found in human, Drosphila and yeast proteins," Nucl. Acids Res. 20:2603 (1992).

Hodges et al., "Structure, organization, and dynamics of promyelocytic leukemia protein nuclear bodies," Am. J. Hum. Genet. 63:297-304 (1998).

Ishov et al., "Human cytomegalovirus immediate early interaction with host nuclear structures: definition of an immediate transcript environnment," J. Cell. Biol 138:5-16 (1997).

Jeanmougin et al., "The bromodomain revisited," Trends Biochem. Sci. 22:151-153 (1997).

Kadereit et al., "Molecular cloning of two new interferon-induced, highly related nuclear phosphoproteins," J. Biol. Chem. 268:24432-2441 (1993).

Kersten et al., "Peroxisome proliferator activated receptor $\alpha$ mediates the adaptive response to fasting," J. Clin. Invest. 103:1489-1498 (1999).

LaMorte et al., "Localization of nascent RNA and CREB binding protein with the PML-containing nuclear body," Proc. Natl. Acad. Sci. USA 95:4991-4996 (1998).

Laurent et al., "The yeast SNF2/SWI2 protein has DNA-stimulated ATPase activity required for transcriptional activation," Genes Dev. 7:583-591 (1993).

Le Douarin et al., "A possible involvement of TIF1 alpha and TIF1 beta in the epigenetic control of transcription by nuclear receptors," EMBO J. 15:6701-6715 (1996).

Lehming et al., "Chromatin components as part of a putative transcriptional repressing complex," Proc. Natl. Acad. Sci. USA 95:7322-7326 (1998).

Mahl et al., "Primary biliary cirrhosis: survival of a large cohort of symptomatic and asymptomatic patients followed for 24 years," J. Hepatol. 20:707-713 (1994).

Melnick et al., "Deconstructing a disease: RARalpha, its fusion partners, and their roles in the pathogenesis of acute promyelocytic leukemia," Blood 93:3167-3215 (1999).

Nagamine et al., "Positional cloning of the APECED gene," Nature Genetics 17:393-397 (1997).

Quignon et al., "PML induces a novel caspase-independent death process," Nature Genetics 10:259-265 (1998).

Seeler et al., "Interaction of SP100 with HP1 proteins: a link between the promyelocytic leukemia-associated nuclear bodies and the chromatin compartment," Proc. Natl. Acad. Sci. USA 95:7316-7321 (1998).

Smith et al., "Single-step purification of polypeptides expressed in *Escherichia coli* as fusions with glutathione S-transferase," Gene 67:31-40 (1988).

Springer et al., "Asymptomatic primary biliary cirrhosis: a study of its natural history and prognosis," Am. J. Gastroenterol. 94:47-53 (1999).

Sternsdorf et al., "Nuclear dots: actors on many stages," Immunobiology 198:307-331 (1997).

Szostecki et al., "Isolation and characterization of cDNA encoding a human nuclear antigen predominantly recognized by autoantibodies from patients with primary biliary cirrhosis," J. Immunol. 145:4338-4347 (1990).

Wang et al., "Role of PML in Cell Growth and the Retinoic Acid Pathway," Science 279:1547-1551 (1998).

Wang et al., "PML is essential for multiple apoptotic pathways," Nature Genetics 20:266-272 (1998).

* cited by examiner sp110.genbank  Length: 2336   June 20, 19100  11:13
Type: N  Check: 2745  ..

```
   1  TGTAACTCTC CCAATCTTGA GGAGTGATCC CTGTCCCAGC CCTGGAAAG
  51  CGAGGAACGA CAAACTCAAA GTCCAGGATG TTCACCATGA CAAGAGCCAT
 101  GGAAGAGGCT CTTTTTCAGC ACTTCATGCA CCAGAAGCTG GGGATCGCCT
 151  ATGCCATACA CAAGCCATTT CCCTTCTTTG AAGGCCTCCT AGACAACTCC
 201  ATCATCACTA AGAGAATGTA CATGGAATCT CTGGAAGCCT GTAGAAATTT
 251  GATCCCTGTA TCCAGAGTGG TGCACAACAT TCTCACCCAA CTGGAGAGGA
 301  CTTTTAACCT GTCTCTTCTG GTGACATTGT TCAGTCAAAT TAACCTGCGT
 351  GAATATCCCA ATCTGGTGAC GATTTACAGA AGCTTCAAAC GTGTTGGTGC
 401  TTCCTATGAA CGGCAGAGCA GAGACACACC AATCCTACTT GAAGCCCCAA
 451  CTGGCCTAGC AGAAGGAAGC TCcCTCCATA CCCCACTGGC GCTgccccac
 501  cacaaacccc ctcaaccaag ctgttcaccc tgtgcgccaa gagtcagtga
 551  gcctggaaca tcctcccagc aaagcactga gatcctgagt gagtcgccca
 601  gcccatctga ccctgtcctg cctctccctg cactcatcca ggaaggaaga
 651  agcacttcag tgaccaatga caagttaaca tccaaaatga atgcggaaga
 701  agactcagaa gagatgccca gcctcctcac tagcactgtg caagtggcca
 751  gtgacaacct gatccccaa ataagagata agaagaccc tcaagagatg
 801  ccccactctc ccttgggctc tatgccagag ataagagata attctccaga
 851  accaaatgac cagaagagc cccaggaggt gtccagcaca ccttcagacA
 901  AGAAAGGAAA GAAAAGAAAA AGATGTATCT GGTCAACTCC AAAAAGGAGA
 951  CATAAGAAAA AAAGCCTCCC AAGAGGGACA GCCTCATCTA GACACGGAAT
1001  CCAAAAGAAG CTCAAAAGGG TGGATCAGGT TCCTCAAAAG AAAGATGACT
1051  CAACTTGTAA CTCCACGGTA GAGACAAGGG CCCAAAAGGC GAGAACTGAA
1101  TGTGCCCGAA AGTCGAGATC AGAGGAGATC ATTGATGGCA CTTCAGAAAT
1151  GAATGAAGGA AAGAGGTCCC AGAAGACGCC TAGTACACCA CGAAGGGTCA
1201  CACAAGGGGC AGCCTCACCT GGGCATGGCA TCCAAGAGAA GCTCCAAGTG
1251  GTGGATAAGG TGACTCAAAG GAAAGACGAC TCAACCTGGA ACTCAGAGGT
```

FIG. 1A

```
1301  CATGATGAGG GTCCAAAAGG CAAGAACTAA ATGTGCCCGA AAGTCCAGAT

1351  CGAAAGAAAA GAAAAAGGAG AAAGATATCT GTTCAAGCTC AAAAAGGAGA

1401  TTTCAGAAAA ATATTCACCG AAGAGGAAAA CCCAAAAGTG ACACTGTGGA

1451  TTTTCACTGT TCTAAGCTCC CCGTGACCTG TGGTGAGGCG AAAGGGATTT

1501  TATATAAGAA GAAAATGAAA CACGGATCCT CAGTGAAGTG CATTCGGAAT

1551  GAGGATGGAA CTTGGTTAAC ACCAAATGAA TTTGAAGTCG AAGGAAAAGG

1601  AAGGAACGCA AAGAACTGGA ACGGAATAT ACGTTGTGAA GGAAcGACCC

1651  TAGGAGAGCT GCTGAAGCGG AAAAACTCGG ATGAATGCGA GGTGTGCTGT

1701  CAAGGGGGAC AACTTCTCTG CTGCGGtACT TGTCCACGAG TCTTCCATGA

1751  GGACTGTCAC ATCCCCCCTG TGGAAGCCAA GAGGATGCTG TGGAGTTGCA

1801  CCTTCTGCAG GATgAAGAGG TCTTCAGGAA GCCAACAGTG CCATCATGTA

1851  TCTAAGACCC TGGAGAGGCA GATGCAGCCT CAGGACCAGC TGAttcgAGA

1901  TTACGGTGAG cCCTTTCAGG AAGCAATGTG GTTGGACCTG GTTAAGGAAA

1951  GGCTGATTAC GGAAATGTAC ACGGTGGCAT GGTTTGTGCG AGACATGCGC

2001  CTGATGTTTC GCAACCATAA AACATTTTAC AAGGCTTCTG ACTTTGGCCA

2051  GGTAGGACTT GACTTAGAGG CAGAATTTGA AAAAGATCTC AAAGACGTGC

2101  TCGGTTTTCA TGAAGCCAAT GACGGCGGTT TCtggactct tccttgaccc 2151  tgttctgtaa agactgaagc atccccgacc tcaggattca gctgatggga 2201  ccctggcttg gactgttgat tgccagtgag tctgggatgt aattggctgc 2251  cctcaggacc caaacccaga cacttcatag gattatcaca ccctccatct 2301  ttattctttc tttttacctt taaaagtcta tatcta
```

```
                                                                                              SP100-LIKE DOMAIN
SP110                                                                        MFTMTR AMEEAL FQHFMHQKL GIAYAI HKPFPFFEGL LDNSI I TKRMYMESLE       53
SP140    MAQQGQQGQGQMASGDSNL NFRMVAEI QNVEGQNL QEQVCPEPI FRFFRENKVEI ASAI TRPFPFLMGLRDRSFI SEQMYEHFQE    83

SP100-LIKE DOMAIN
SP110    ACRNLI PVSRVVHNI LTQLERTFNL SLLVTLFSQI NLREYPNLVTI YRSFKRVGASYE. RQSRDTPI LLEAPTGLAEGSSLHTPLALPHHKPPQPSCSPC       152
SP140    AFRNLVPVTVRVMYCVL SELEKTFGMSHLEALFSRI NLMAYPDLNEI YRSFQNVCYEHSPLQMNVVNDLEDRPRLLPYGKQENSNACHEMDDI AVPQEALS         183

SP110    APRVSEPGTSSQQSTEI LSESPSPSDPVLPLPALI QEGRSTSVTNDKLTSKMNAEEDSEEMPSLLTSTVQVASDNLI PQI RDKEDPQEMPHSPLGSMPEI           252
SP140    SSPRCEPGFSS. ESCEQLALPKAGGGDAEDAPSLLPVSCKLAI QI D.........EGESEEMPKLLPYDTEETFDLKTPQVTNEGEPEKGLCLLPGEGEEG          274

SP110    RDNSPEPNDPEEPQEVSSTPSDKKGKKRRCI WSTPKRRHKKKSLPRGTASSRHGI QKKLKRVDQVPQKKDDSTCNSTVETRAQKARTECARKSRSEEI I             352
SP140    SDDCSEMCDGEERQEASSSLA. RRGSVSSELENHPMNEEGESEEL... ASSLLYDNVPGAEQSAYENEKCSCVMCFSEEVPGSPEARTESDQACGTMDTV            370

SAND DOMAIN
SP110    DGTSEMNEGKRSQKTPSTPRRVTQGAASPGHGI QEKLQVVDKVTQRKDDSTWNSEVMVRVQKART... KCARKSRSKEKKEKDI CSSSKRRFQKNI HRRG          450
SP140    DI ANNSTLGK...... PKRKRRKKR...... GHGMGMSRMRMRRQKNSQQNDNSKADGQVVSSEKKANVNLKDLSKI RGRKRGKPGTRFTQSDRAAQKVRSRA       460

SP110    ..KPKSDTVDFHCSKLPVTCGEAKGI LYKKKMKHGSSVKCI RNEDGTWLTPNEFEVEGKGRNAKNWKRNI RCEGTTLGELLIKRK...........                532
SP140    SRKHKDETVDFKAPLLPVTCGGVKGI LHKKKLQQGI LVKCI QTEDGKWFTPTEFEI KCGHARSKNWRLSVRCGGMPLRWLMENGFLPDPPRI RYRKKKRI           560

PLANT HOMEOBOX DOMAIN
SP110    ...........NSDECEVCCQGQQLLCCGTCPRVFHEDCHI PPVEAKRMLWSCTFQRMKRSSSGQQCHHVSKTLERQMQPQDQL............                605
SP140    LKSQNNSSVDPCMRNLDECEVCRDGGELFCCDTCSRVFHEDCHI PPVEAERTPWNCI FQRMKESPGSQQCCQESEVLERCMCPEEQLKCEFLLLKVYCCS             660

BROMODOMAIN
                     HELIX A                                HELIX B                                HELIX C
SP110    ........I RDYGEPFQEAMMLDLVKERLI TEMY.. TVANEVRDMRLMERNHKTFYKASDFGQVGLDLEAEFEKDLKDVLGFHEANDGGFWTLP                 689
SP140    ESSFFAKI PYYYYI REACQGLKEPMWLDKI KKRLNEHGYPQVEGFVQDMRLI FQNHRASYKYKDFGQMGFRLEAEFEKNFKEVFAI QETNGNN                753
```

(Linear) MAP of: sp110.genbank  check: 2745  from: 1 to: 2336

June 20, 19100 11:14 ..

```
      TGTAACTCTCCCAATCTTGAGGAGTGATCCCTGTCCCAGCCCCTGGAAAGCGAGGAACGA
    1 ---------+---------+---------+---------+---------+---------+ 60
      ACATTGAGAGGGTTAGAACTCCTCACTAGGGACAGGGTCGGGGACCTTTCGCTCCTTGCT
``` a     C  N  S  P  N  L  E  E  *  S  L  S  Q  P  L  E  S  E  E  R  -
b      V  T  L  P  I  L  R  S  D  P  C  P  S  P  W  K  A  R  N  D -
c       *  L  S  Q  S  *  G  V  I  P  V  P  A  P  G  K  R  G  T  T -

```
      CAAACTCAAAGTCCAGGATGTTCACCATGACAAGAGCCATGGAAGAGGCTCTTTTTCAGC
   61 ---------+---------+---------+---------+---------+---------+ 120
      GTTTGAGTTTCAGGTCCTACAAGTGGTACTGTTCTCGGTACCTTCTCCGAGAAAAAGTCG
``` a     Q  T  Q  S  P  G  C  S  P  *  Q  E  P  W  K  R  L  F  F  S  -
b      K  L  K  V  Q  D  V  H  H  D  K  S  H  G  R  G  S  F  S  A -
c       N  S  K  S  R  M  F  T  M  T  R  A  M  E  E  A  L  F  Q  H -

```
      ACTTCATGCACCAGAAGCTGGGGATCGCCTATGCCATACACAAGCCATTTCCCTTCTTTG
  121 ---------+---------+---------+---------+---------+---------+ 180
      TGAAGTACGTGGTCTTCGACCCCTAGCGGATACGGTATGTGTTCGGTAAAGGGAAGAAAC
``` a     T  S  C  T  R  S  W  G  S  P  M  P  Y  T  S  H  F  P  S  L  -
b      L  H  A  P  E  A  G  D  R  L  C  H  T  Q  A  I  S  L  L  * -
c       F  M  H  Q  K  L  G  I  A  Y  A  I  H  K  P  F  P  F  F  E -

```
      AAGGCCTCCTAGACAACTCCATCATCACTAAGAGAATGTACATGGAATCTCTGGAAGCCT
  181 ---------+---------+---------+---------+---------+---------+ 240
      TTCCGGAGGATCTGTTGAGGTAGTAGTGATTCTCTTACATGTACCTTAGAGACCTTCGGA
``` a     K  A  S  *  T  T  P  S  S  L  R  E  C  T  W  N  L  W  K  P  -
b      R  P  P  R  Q  L  H  H  H  *  E  N  V  H  G  I  S  G  S  L -
c       G  L  L  D  N  S  I  I  T  K  R  M  Y  M  E  S  L  E  A  C -

```
      GTAGAAATTTGATCCCTGTATCCAGAGTGGTGCACAACATTCTCACCCAACTGGAGAGGA
  241 ---------+---------+---------+---------+---------+---------+ 300
      CATCTTTAAACTAGGGACATAGGTCTCACCACGTGTTGTAAGAGTGGGTTGACCTCTCCT
``` a     V  E  I  *  S  L  Y  P  E  W  C  T  T  F  S  P  N  W  R  G  -
b      *  K  F  D  P  C  I  Q  S  G  A  Q  H  S  H  P  T  G  E  D -
c       R  N  L  I  P  V  S  R  V  V  H  N  I  L  T  Q  L  E  R  T -

```
      CTTTTAACCTGTCTCTTCTGGTGACATTGTTCAGTCAAATTAACCTGCGTGAATATCCCA
  301 ---------+---------+---------+---------+---------+---------+ 360
      GAAAATTGGACAGAGAAGACCACTGTAACAAGTCAGTTTAATTGGACGCACTTATAGGGT
``` a     L  L  T  C  L  F  W  *  H  C  S  V  K  L  T  C  V  N  I  P  -
b      F  *  P  V  S  S  G  D  I  V  Q  S  N  *  P  A  *  I  S  Q -
c       F  N  L  S  L  L  V  T  L  F  S  Q  I  N  L  R  E  Y  P  N -

FIG. 3A

```
        ATCTGGTGACGATTTACAGAAGCTTCAAACGTGTTGGTGCTTCCTATGAACGGCAGAGCA
    361 ---------+---------+---------+---------+---------+---------+ 420
        TAGACCACTGCTAAATGTCTTCGAAGTTTGCACAACCACGAAGGATACTTGCCGTCTCGT
``` a     I   W   *   R   F   T   E   A   S   N   V   L   V   L   P   M   N   G   R   A   -
b       S   G   D   D   L   Q   K   L   Q   T   C   W   C   F   L   *   T   A   E   Q   -
c         L   V   T   I   Y   R   S   F   K   R   V   G   A   S   Y   E   R   Q   S   R   -

```
        GAGACACACCAATCCTACTTGAAGCCCCAACTGGCCTAGCAGAAGGAAGCTCcCTCCATA
    421 ---------+---------+---------+---------+---------+---------+ 480
        CTCTGTGTGGTTAGGATGAACTTCGGGGTTGACCGGATCGTCTTCCTTCGAGgGAGGTAT
``` a     E   T   H   Q   S   Y   L   K   P   Q   L   A   *   Q   K   E   A   P   S   I   -
b       R   H   T   N   P   T   *   S   P   N   W   P   S   R   R   K   L   P   P   Y   -
c         D   T   P   I   L   L   E   A   P   T   G   L   A   E   G   S   S   L   H   T   -

```
        CCCCACTGGCGCTgccccaccacaaacccctcaaccaagctgttcaccctgtgcgccaa
    481 ---------+---------+---------+---------+---------+---------+ 540
        GGGGTGACCGCGAcggggtggtgtttgggggagttggttcgacaagtgggacacgcggtt
``` a     P   H   W   R   C   P   T   T   N   P   L   N   Q   A   V   H   P   V   R   Q   -
b       P   T   G   A   A   P   P   Q   T   P   S   T   K   L   F   T   L   C   A   K   -
c         P   L   A   L   P   H   H   K   P   P   Q   P   S   C   S   P   C   A   P   R   -

```
        gagtcagtgagcctggaacatcctcccagcaaagcactgagatcctgagtgagtcgccca
    541 ---------+---------+---------+---------+---------+---------+ 600
        ctcagtcactcggaccttgtaggagggtcgtttcgtgactctaggactcactcagcgggt
``` a     E   S   V   S   L   E   H   P   P   S   K   A   L   R   S   *   V   S   R   P   -
b       S   Q   *   A   W   N   I   L   P   A   K   H   *   D   P   E   *   V   A   Q   -
c         V   S   E   P   G   T   S   S   Q   Q   S   T   E   I   L   S   E   S   P   S   -

```
        gcccatctgaccctgtcctgcctctccctgcactcatccaggaaggaagaagcacttcag
    601 ---------+---------+---------+---------+---------+---------+ 660
        cgggtagactgggacaggacggagagggacgtgagtaggtccttccttcttcgtgaagtc
``` a     A   H   L   T   L   S   C   L   S   L   H   S   S   R   K   E   E   A   L   Q   -
b       P   I   *   P   C   P   A   S   P   C   T   H   P   G   R   K   K   H   F   S   -
c         P   S   D   P   V   L   P   L   P   A   L   I   Q   E   G   R   S   T   S   V   -

```
        tgaccaatgacaagttaacatccaaaatgaatgcggaagaagactcagaagagatgccca
    661 ---------+---------+---------+---------+---------+---------+ 720
        actggttactgttcaattgtaggttttacttacgccttcttctgagtcttctctacgggt
``` a     *   P   M   T   S   *   H   P   K   *   M   R   K   K   T   Q   K   R   C   P   -
b       D   Q   *   Q   V   N   I   Q   N   E   C   G   R   R   L   R   R   D   A   Q   -
c         T   N   D   K   L   T   S   K   M   N   A   E   E   D   S   E   E   M   P   S   -

FIG. 3B

```
          gcctcctcactagcactgtgcaagtggccagtgacaacctgatcccccaaataagagata
     721  ---------+---------+---------+---------+---------+---------+ 780
          cggaggagtgatcgtgacacgttccggtcactgttggactagggggtttattctctat
``` a    A S S L A L C K W P V T T * S P K * E I -
b      P P H * H C A S G Q * Q P D P P N K R * -
c        L L T S T V Q V A S D N L I P Q I R D K -

```
          aagaagaccctcaagagatgccccactctcccttgggctctatgccagagataagagata
     781  ---------+---------+---------+---------+---------+---------+ 840
          ttcttctgggagttctctacggggtgagagggaacccgagatacggtctctattctctat
``` a    K K T L K R C P T L P W A L C Q R * E I -
b      R R P S R D A P L S L G L Y A R D K R * -
c        E D P Q E M P H S P L G S M P E I R D N -

```
          attctccagaaccaaatgacccagaagagccccaggaggtgtccagcacaccttcagacA
     841  ---------+---------+---------+---------+---------+---------+ 900
          taagaggtcttggtttactgggtcttctcggggtcctccacaggtcgtgtggaagtctgT
``` a    I L Q N Q M T Q K S P R R C P A H L Q T -
b      F S R T K * P R R A P G G V Q H T F R Q -
c        S P E P N D P E E P Q E V S S T P S D K -

```
          AGAAAGGAAAGAAAAGAAAAAGATGTATCTGGTCAACTCCAAAAAGGAGACATAAGAAAA
     901  ---------+---------+---------+---------+---------+---------+ 960
          TCTTTCCTTTCTTTTCTTTTTCTACATAGACCAGTTGAGGTTTTTCCTCTGTATTCTTTT
``` a    R K E R K E K D V S G Q L Q K G D I R K -
b      E R K E K K K M Y L V N S K K E T * E K -
c        K G K K R K R C I W S T P K R R H K K K -

```
          AAAGCCTCCCAAGAGGGACAGCCTCATCTAGACACGGAATCCAAAAGAAGCTCAAAAGGG
     961  ---------+---------+---------+---------+---------+---------+ 1020
          TTTCGGAGGGTTCTCCCTGTCGGAGTAGATCTGTGCCTTAGGTTTTCTTCGAGTTTTCCC
``` a    K A S Q E G Q P H L D T E S K R S S K G -
b      K P P K R D S L I * T R N P K E A Q K G -
c        S L P R G T A S S R H G I Q K K L K R V -

```
          TGGATCAGGTTCCTCAAAAGAAAGATGACTCAACTTGTAACTCCACGGTAGAGACAAGGG
    1021  ---------+---------+---------+---------+---------+---------+ 1080
          ACCTAGTCCAAGGAGTTTTCTTTCTACTGAGTTGAACATTGAGGTGCCATCTCTGTTCCC
``` a    W I R F L K R K M T Q L V T P R * R Q G -
b      G S G S S K E R * L N L * L H G R D K G -
c        D Q V P Q K K D D S T C N S T V E T R A -

FIG. 3C

```
        CCCAAAAGGCGAGAACTGAATGTGCCCGAAAGTCGAGATCAGAGGAGATCATTGATGGCA
   1081 ---------+---------+---------+---------+---------+---------+ 1140
        GGGTTTTCCGCTCTTGACTTACACGGGCTTTCAGCTCTAGTCTCCTCTAGTAACTACCGT a         P  K  R  R  E  L  N  V  P  E  S  R  D  Q  R  R  S  L  M  A  -
b          P  K  G  E  N  *  M  C  P  K  V  E  I  R  G  D  H  *  W  H -
c           Q  K  A  R  T  E  C  A  R  K  S  R  S  E  E  I  I  D  G  T -

CTTCAGAAATGAATGAAGGAAAGAGGTCCCAGAAGACGCCTAGTACACCACGAAGGGTCA
   1141 ---------+---------+---------+---------+---------+---------+ 1200
        GAAGTCTTTACTTACTTCCTTTCTCCAGGGTCTTCTGCGGATCATGTGGTGCTTCCCAGT a         L  Q  K  *  M  K  E  R  G  P  R  R  R  L  V  H  H  E  G  S  -
b          F  R  N  E  *  R  K  E  V  P  E  D  A  *  Y  T  T  K  G  H -
c           S  E  M  N  E  G  K  R  S  Q  K  T  P  S  T  P  R  R  V  T -

CACAAGGGGCAGCCTCACCTGGGCATGGCATCCAAGAGAAGCTCCAAGTGGTGGATAAGG
   1201 ---------+---------+---------+---------+---------+---------+ 1260
        GTGTTCCCCGTCGGAGTGGACCCGTACCGTAGGTTCTCTTCGAGGTTCACCACCTATTCC a         H  K  G  Q  P  H  L  G  M  A  S  K  R  S  S  K  W  W  I  R  -
b          T  R  G  S  L  T  W  A  W  H  P  R  E  A  P  S  G  G  *  G -
c           Q  G  A  A  S  P  G  H  G  I  Q  E  K  L  Q  V  V  D  K  V -

TGACTCAAAGGAAAGACGACTCAACCTGGAACTCAGAGGTCATGATGAGGGTCCAAAAGG
   1261 ---------+---------+---------+---------+---------+---------+ 1320
        ACTGAGTTTCCTTTCTGCTGAGTTGGACCTTGAGTCTCCAGTACTACTCCCAGGTTTTCC a         *  L  K  G  K  T  T  Q  P  G  T  Q  R  S  *  *  G  S  K  R  -
b          D  S  K  E  R  R  R  L  N  L  E  L  R  G  H  D  E  G  P  K  G -
c           T  Q  R  K  D  D  S  T  W  N  S  E  V  M  M  R  V  Q  K  A -

CAAGAACTAAATGTGCCCGAAAGTCCAGATCGAAAGAAAAGAAAAAGGAGAAAGATATCT
   1321 ---------+---------+---------+---------+---------+---------+ 1380
        GTTCTTGATTTACACGGGCTTTCAGGTCTAGCTTTCTTTTCTTTTTCCTCTTTCTATAGA a         Q  E  L  N  V  P  E  S  P  D  R  K  K  R  K  R  R  K  I  S  -
b          K  N  *  M  C  P  K  V  Q  I  E  R  K  E  K  G  E  R  Y  L -
c           R  T  K  C  A  R  K  S  R  S  K  E  K  K  K  E  K  D  I  C -

GTTCAAGCTCAAAAAGGAGATTTCAGAAAAATATTCACCGAAGAGGAAAACCCAAAAGTG
   1381 ---------+---------+---------+---------+---------+---------+ 1440
        CAAGTTCGAGTTTTTCCTCTAAAGTCTTTTTATAAGTGGCTTCTCCTTTTGGGTTTTCAC a         V  Q  A  Q  K  G  D  F  R  K  I  F  T  E  E  E  N  P  K  V  -
b          F  K  L  K  K  E  I  S  E  K  Y  S  P  K  R  K  T  Q  K  * -
c           S  S  S  K  R  R  F  Q  K  N  I  H  R  R  G  K  P  K  S  D -
```

FIG. 3D

```
        ACACTGTGGATTTTCACTGTTCTAAGCTCCCCGTGACCTGTGGTGAGGCGAAAGGGATTT
   1441 ---------+---------+---------+---------+---------+---------+ 1500
        TGTGACACCTAAAAGTGACAAGATTCGAGGGGCACTGGACACCACTCCGCTTTCCCTAAA a       T  L  W  I  F  T  V  L  S  S  P  *  P  V  V  R  R  K  G  F   -
b        H  C  G  F  S  L  F  *  A  P  R  D  L  W  *  G  E  R  D  F  -
c         T  V  D  F  H  C  S  K  L  P  V  T  C  G  E  A  K  G  I  L -

TATATAAGAAGAAAATGAAACACGGATCCTCAGTGAAGTGCATTCGGAATGAGGATGGAA
   1501 ---------+---------+---------+---------+---------+---------+ 1560
        ATATATTCTTCTTTTACTTTGTGCCTAGGAGTCACTTCACGTAAGCCTTACTCCTACCTT a       Y  I  R  R  K  *  N  T  D  P  Q  *  S  A  F  G  M  R  M  E   -
b        I  *  E  E  N  E  T  R  I  L  S  E  V  H  S  E  *  G  W  N  -
c         Y  K  K  K  M  K  H  G  S  S  V  K  C  I  R  N  E  D  G  T -

CTTGGTTAACACCAAATGAATTTGAAGTCGAAGGAAAAGGAAGGAACGCAAAGAACTGGA
   1561 ---------+---------+---------+---------+---------+---------+ 1620
        GAACCAATTGTGGTTTACTTAAACTTCAGCTTCCTTTTCCTTCCTTGCGTTTCTTGACCT a       L  G  *  H  Q  M  N  L  K  S  K  E  K  E  G  T  Q  R  T  G   -
b        L  V  N  T  K  *  I  *  S  R  R  K  R  K  E  R  K  E  L  E  -
c         W  L  T  P  N  E  F  E  V  E  G  K  G  R  N  A  K  N  W  K -

AACGGAATATACGTTGTGAAGGAAcGACCCTAGGAGAGCTGCTGAAGCGGAAAAACTCGG
   1621 ---------+---------+---------+---------+---------+---------+ 1680
        TTGCCTTATATGCAACACTTCCTTgCTGGGATCCTCTCGACGACTTCGCCTTTTTGAGCC a       N  G  I  Y  V  V  K  E  R  P  *  E  S  C  *  S  G  K  T  R   -
b        T  E  Y  T  L  *  R  N  D  P  R  R  A  A  E  A  E  K  L  G  -
c         R  N  I  R  C  E  G  T  T  L  G  E  L  L  K  R  K  N  S  D -

ATGAATGCGAGGTGTGCTGTCAAGGGGGACAACTTCTCTGCTGCGGtACTTGTCCACGAG
   1681 ---------+---------+---------+---------+---------+---------+ 1740
        TACTTACGCTCCACACGACAGTTCCCCCTGTTGAAGAGACGACGCCaTGAACAGGTGCTC a       M  N  A  R  C  A  V  K  G  D  N  F  S  A  A  V  L  V  H  E   -
b        *  M  R  G  V  L  S  R  G  T  T  S  L  L  R  Y  L  S  T  S  -
c         E  C  E  V  C  C  Q  G  G  Q  L  L  C  C  G  T  C  P  R  V -

TCTTCCATGAGGACTGTCACATCCCCCCTGTGGAAGCCAAGAGGATGCTGTGGAGTTGCA
   1741 ---------+---------+---------+---------+---------+---------+ 1800
        AGAAGGTACTCCTGACAGTGTAGGGGGGACACCTTCGGTTCTCCTACGACACCTCAACGT a       S  S  M  R  T  V  T  S  P  L  W  K  P  R  G  C  C  G  V  A   -
b        L  P  *  G  L  S  H  P  P  C  G  S  Q  E  D  A  V  E  L  H  -
c         F  H  E  D  C  H  I  P  P  V  E  A  K  R  M  L  W  S  C  T -
```

FIG. 3E

```
        CCTTCTGCAGGATgAAGAGGTCTTCAGGAAGCCAACAGTGCCATCATGTATCTAAGACCC
 1801   ---------+---------+---------+---------+---------+---------+ 1860
        GGAAGACGTCCTAcTTCTCCAGAAGTCCTTCGGTTGTCACGGTAGTACATAGATTCTGGG
``` a     P  S  A  G  *  R  G  L  Q  E  A  N  S  A  I  M  Y  L  R  P  -
b      L  L  Q  D  E  E  V  F  R  K  P  T  V  P  S  C  I  *  D  P -
c       F  C  R  M  K  R  S  S  G  S  Q  Q  C  H  H  V  S  K  T  L-

```
        TGGAGAGGCAGATGCAGCCTCAGGACCAGCTGAttcgAGATTACGGTGAGcCCTTTCAGG
 1861   ---------+---------+---------+---------+---------+---------+ 1920
        ACCTCTCCGTCTACGTCGGAGTCCTGGTCGACTaagcTCTAATGCCACTCgGGAAAGTCC
``` a     W  R  G  R  C  S  L  R  T  S  *  F  E  I  T  V  S  P  F  R  -
b      G  E  A  D  A  A  S  G  P  A  D  S  R  L  R  *  A  L  S  G -
c       E  R  Q  M  Q  P  Q  D  Q  L  I  R  D  Y  G  E  P  F  Q  E-

```
        AAGCAATGTGGTTGGACCTGGTTAAGGAAAGGCTGATTACGGAAATGTACACGGTGGCAT
 1921   ---------+---------+---------+---------+---------+---------+ 1980
        TTCGTTACACCAACCTGGACCAATTCCTTTCCGACTAATGCCTTTACATGTGCCACCGTA
``` a     K  Q  C  G  W  T  W  L  R  K  G  *  L  R  K  C  T  R  W  H  -
b      S  N  V  V  G  P  G  *  G  K  A  D  Y  G  N  V  H  G  G  M -
c       A  M  W  L  D  L  V  K  E  R  L  I  T  E  M  Y  T  V  A  W-

```
        GGTTTGTGCGAGACATGCGCCTGATGTTTCGCAACCATAAAACATTTTACAAGGCTTCTG
 1981   ---------+---------+---------+---------+---------+---------+ 2040
        CCAAACACGCTCTGTACGCGGACTACAAAGCGTTGGTATTTTGTAAAATGTTCCGAAGAC
``` a     G  L  C  E  T  C  A  *  C  F  A  T  I  K  H  F  T  R  L  L  -
b      V  C  A  R  H  A  P  D  V  S  Q  P  *  N  I  L  Q  G  F  * -
c       F  V  R  D  M  R  L  M  F  R  N  H  K  T  F  Y  K  A  S  D-

```
        ACTTTGGCCAGGTAGGACTTGACTTAGAGGCAGAATTTGAAAAAGATCTCAAAGACGTGC
 2041   ---------+---------+---------+---------+---------+---------+ 2100
        TGAAACCGGTCCATCCTGAACTGAATCTCCGTCTTAAACTTTTTCTAGAGTTTCTGCACG
``` a     T  L  A  R  *  D  L  T  *  R  Q  N  L  K  K  I  S  K  T  C  -
b      L  W  P  G  R  T  *  L  R  G  R  I  *  K  R  S  Q  R  R  A -
c       F  G  Q  V  G  L  D  L  E  A  E  F  E  K  D  L  K  D  V  L-

```
        TCGGTTTTCATGAAGCCAATGACGGCGGTTTCtggactcttccttgaccctgttctgtaa
 2101   ---------+---------+---------+---------+---------+---------+ 2160
        AGCCAAAAGTACTTCGGTTACTGCCGCCAAAGacctgagaaggaactgggacaagacatt
``` a     S  V  F  M  K  P  M  T  A  V  S  G  L  F  L  D  P  V  L  *  -
b      R  F  S  *  S  Q  *  R  R  F  L  D  S  S  L  T  L  F  C  K -
c       G  F  H  E  A  N  D  G  G  F  W  T  L  P  *  P  C  S  V  K-

```
        agactgaagcatccccgacctcaggattcagctgatgggaccctggcttggactgttgat
 2161   ---------+---------+---------+---------+---------+---------+ 2220
        tctgacttcgtaggggctggagtcctaagtcgactacccctgggaccgaacctgacaacta
```

FIG. 3F

```
a      R  L  K  H  P  R  P  Q  D  S  A  D  G  T  L  A  W  T  V  D  -
b      D  *  S  I  P  D  L  R  I  Q  L  M  G  P  W  L  G  L  L  I  -
c         T  E  A  S  P  T  S  G  F  S  *  W  D  P  G  L  D  C  *  L  - tgccagtgagtctgggatgtaattggctgccctcaggacccaaacccagacacttcatag
     2221  ---------+---------+---------+---------+---------+---------+ 2280
           acggtcactcagaccctacattaaccgacgggagtcctgggtttgggtctgtgaagtatc a      C  Q  *  V  W  D  V  I  G  C  P  Q  D  P  N  P  D  T  S  *  -
b      A  S  E  S  G  M  *  L  A  A  L  R  T  Q  T  Q  T  L  H  R  -
c         P  V  S  L  G  C  N  W  L  P  S  G  P  K  P  R  H  F  I  G  - gattatacacaccctccatctttattctttcttttacctttaaaagtctatatcta
     2281  ---------+---------+---------+---------+---------+------ 2336
           ctaatagtgtgggaggtagaaataagaaagaaaaatggaaattttcagatatagat a      D  Y  H  T  L  H  L  Y  S  F  F  L  P  L  K  V  Y  I     -
b      I  I  T  P  S  I  F  I  L  S  F  Y  L  *  K  S  I  S     -
c         L  S  H  P  P  S  L  F  F  L  F  T  F  K  S  L  Y  L  -
```

FIG. 3G (Linear) MAP of: sp110b.  check: 2812  from: 1  to: 1919

June 20, 19100 10:42  ..

```
        TGTAACTCTCCCAATCTTGAGGAGTGATCCCTGTCCCAGCCCCTGGAAAGCGAGGAACGA
    1   ---------+---------+---------+---------+---------+---------+ 60
        ACATTGAGAGGGTTAGAACTCCTCACTAGGGACAGGGTCGGGGACCTTTCGCTCCTTGCT
``` a     C  N  S  P  N  L  E  E  \*  S  L  S  Q  P  L  E  S  E  E  R  -
b       V  T  L  P  I  L  R  S  D  P  C  P  S  P  W  K  A  R  N  D  -
c         \*  L  S  Q  S  \*  G  V  I  P  V  P  A  P  G  K  R  G  T  T  -

```
        CAAACTCAAAGTCCAGGATGTTCACCATGACAAGAGCCATGGAAGAGGCTCTTTTTCAGC
   61   ---------+---------+---------+---------+---------+---------+ 120
        GTTTGAGTTTCAGGTCCTACAAGTGGTACTGTTCTCGGTACCTTCTCCGAGAAAAAGTCG
``` a     Q  T  Q  S  P  G  C  S  P  \*  Q  E  P  W  K  R  L  F  F  S  -
b       K  L  K  V  Q  D  V  H  H  D  K  S  H  G  R  G  S  F  S  A  -
c         N  S  K  S  R  M  F  T  M  T  R  A  M  E  E  A  L  F  Q  H  -

```
        ACTTCATGCACCAGAAGCTGGGGATCGCCTATGCCATACACAAGCCATTTCCCTTCTTTG
  121   ---------+---------+---------+---------+---------+---------+ 180
        TGAAGTACGTGGTCTTCGACCCCTAGCGGATACGGTATGTGTTCGGTAAAGGGAAGAAAC
``` a     T  S  C  T  R  S  W  G  S  P  M  P  Y  T  S  H  F  P  S  L  -
b       L  H  A  P  E  A  G  D  R  L  C  H  T  Q  A  I  S  L  L  \*  -
c         F  M  H  Q  K  L  G  I  A  Y  A  I  H  K  P  F  P  F  F  E  -

```
        AAGGCCTCCTAGACAACTCCATCATCACTAAGAGAATGTACATGGAATCTCTGGAAGCCT
  181   ---------+---------+---------+---------+---------+---------+ 240
        TTCCGGAGGATCTGTTGAGGTAGTAGTGATTCTCTTACATGTACCTTAGAGACCTTCGGA
``` a     K  A  S  \*  T  T  P  S  S  L  R  E  C  T  W  N  L  W  K  P  -
b       R  P  P  R  Q  L  H  H  H  \*  E  N  V  H  G  I  S  G  S  L  -
c         G  L  L  D  N  S  I  I  T  K  R  M  Y  M  E  S  L  E  A  C  -

```
        GTAGAAATTTGATCCCTGTATCCAGAGTGGTGCACAACATTCTCACCCAACTGGAGAGGA
  241   ---------+---------+---------+---------+---------+---------+ 300
        CATCTTTAAACTAGGGACATAGGTCTCACCACGTGTTGTAAGAGTGGGTTGACCTCTCCT
``` a     V  E  I  \*  S  L  Y  P  E  W  C  T  T  F  S  P  N  W  R  G  -
b       \*  K  F  D  P  C  I  Q  S  G  A  Q  H  S  H  P  T  G  E  D  -
c         R  N  L  I  P  V  S  R  V  V  H  N  I  L  T  Q  L  E  R  T  -

```
        CTTTTAACCTGTCTCTTCTGGTGACATTGTTCAGTCAAATTAACCTGCGTGAATATCCCA
  301   ---------+---------+---------+---------+---------+---------+ 360
        GAAAATTGGACAGAGAAGACCACTGTAACAAGTCAGTTTAATTGGACGCACTTATAGGGT
``` a     L  L  T  C  L  F  W  \*  H  C  S  V  K  L  T  C  V  N  I  P  -
b       F  \*  P  V  S  S  G  D  I  V  Q  S  N  \*  P  A  \*  I  S  Q  -
c         F  N  L  S  L  L  V  T  L  F  S  Q  I  N  L  R  E  Y  P  N  -

FIG. 4A

```
        ATCTGGTGACGATTTACAGAAGCTTCAAACGTGTTGGTGCTTCCTATGAACGGCAGAGCA
   361  ---------+---------+---------+---------+---------+---------+ 420
        TAGACCACTGCTAAATGTCTTCGAAGTTTGCACAACCACGAAGGATACTTGCCGTCTCGT a       I W * R F T E A S N V L V L P M N G R A   -
b        S G D D L Q K L Q T C W C F L * T A E Q  -
c         L V T I Y R S F K R V G A S Y E R Q S R -

GAGACACACCAATCCTACTTGAAGCCCCAACTGGCCTAGCAGAAGGAAGCTCcCTCCATA
   421  ---------+---------+---------+---------+---------+---------+ 480
        CTCTGTGTGGTTAGGATGAACTTCGGGGTTGACCGGATCGTCTTCCTTCGAGgGAGGTAT a       E T H Q S Y L K P Q L A * Q K E A P S I   -
b        R H T N P T * S P N W P S R R K L P P Y  -
c         D T P I L L E A P T G L A E G S S L H T -

CCCCACTGGCGCTgccccaccacaaaccccctcaaccaagctgttcaccctgtgcgccaa
   481  ---------+---------+---------+---------+---------+---------+ 540
        GGGGTGACCGCGAcggggtggtgtttgggggagttggttcgacaagtgggacacgcggtt a       P H W R C P T T N P L N Q A V H P V R Q   -
b        P T G A A P P Q T P S T K L F T L C A K  -
c         P L A L P H H K P P Q P S C S P C A P R - gagtcagtgagcctggaacatcctcccagcaaagcactgagatcctgagtgagtcgccca
   541  ---------+---------+---------+---------+---------+---------+ 600
        ctcagtcactcggaccttgtaggagggtcgtttcgtgactctaggactcactcagcgggt a       E S V S L E H P P S K A L R S * V S R P   -
b        S Q * A W N I L P A K H * D P E * V A Q  -
c         V S E P G T S S Q Q S T E I L S E S P S - gcccatctgaccctgtcctgcctctccctgcactcatccaggaaggaagaagcacttcag
   601  ---------+---------+---------+---------+---------+---------+ 660
        cgggtagactgggacaggacggagagggacgtgagtaggtccttccttcttcgtgaagtc a       A H L T L S C L S L H S S R K E E A L Q   -
b        P I * P C P A S P C T H P G R K K H F S  -
c         P S D P V L P L P A L I Q E G R S T S V - tgaccaatgacaagttaacatccaaaatgaatgcggaagaagactcagaagagatgccca
   661  ---------+---------+---------+---------+---------+---------+ 720
        actggttactgttcaattgtaggtttacttacgccttcttctgagtcttctctacgggt a       * P M T S * H P K * M R K K T Q K R C P   -
b        D Q * Q V N I Q N E C G R R L R R D A Q  -
c         T N D K L T S K M N A E E D S E E M P S -
```

FIG. 4B

```
          gcctcctcactagcactgtgcaagtggccagtgacaacctgatcccccaaataagagata
      721 ---------+---------+---------+---------+---------+---------+ 780
          cggaggagtgatcgtgacacgttccaccggtcactgttggactagggggtttattctctat
``` a      A   S   S   L   A   L   C   K   W   P   V   T   T   *   S   P   K   *   E   I   -
b        P   P   H   *   H   C   A   S   G   Q   *   Q   P   D   P   P   N   K   R   *   -
c           L   L   T   S   T   V   Q   V   A   S   D   N   L   I   P   Q   I   R   D   K -

```
          aagaagaccctcaagagatgccccactctcccttgggctctatgccagagataagagata
      781 ---------+---------+---------+---------+---------+---------+ 840
          ttcttctgggagttctctacggggtgagagggaacccgagatacggtctctattctctat
``` a      K   K   T   L   K   R   C   P   T   L   P   W   A   L   C   Q   R   *   E   I   -
b        R   R   P   S   R   D   A   P   L   S   L   G   L   Y   A   R   D   K   R   *   -
c           E   D   P   Q   E   M   P   H   S   P   L   G   S   M   P   E   I   R   D   N -

```
          attctccagaaccaaatgacccagaagagccccaggaggtgtccagcacaccttcagacA
      841 ---------+---------+---------+---------+---------+---------+ 900
          taagaggtcttggtttactgggtcttctcggggtcctccacaggtcgtgtggaagtctgT
``` a      I   L   Q   N   Q   M   T   Q   K   S   P   R   R   C   P   A   H   L   Q   T   -
b        F   S   R   T   K   *   P   R   R   A   P   G   G   V   Q   H   T   F   R   Q   -
c           S   P   E   P   N   D   P   E   E   P   Q   E   V   S   S   T   P   S   D   K -

```
          AGAAAGGAAAGAAAAGAAAAAGATGTATCTGGTCAACTCCAAAAAGGAGACATAAGAAAA
      901 ---------+---------+---------+---------+---------+---------+ 960
          TCTTTCCTTTCTTTTCTTTTTCTACATAGACCAGTTGAGGTTTTTCCTCTGTATTCTTTT
``` a      R   K   E   R   K   E   K   D   V   S   G   Q   L   Q   K   G   D   I   R   K   -
b        E   R   K   E   K   K   K   M   Y   L   V   N   S   K   K   E   T   *   E   K   -
c           K   G   K   K   R   K   R   C   I   W   S   T   P   K   R   R   H   K   K   K -

```
          AAAGCCTCCCAAGAGGGACAGCCTCATCTAGACACGGAATCCAAAAGAAGCTCAAAAGGG
      961 ---------+---------+---------+---------+---------+---------+ 1020
          TTTCGGAGGGTTCTCCCTGTCGGAGTAGATCTGTGCCTTAGGTTTTCTTCGAGTTTTCCC
``` a      K   A   S   Q   E   G   Q   P   H   L   D   T   E   S   K   R   S   S   K   G   -
b        K   P   P   K   R   D   S   L   I   *   T   R   N   P   K   E   A   Q   K   G   -
c           S   L   P   R   G   T   A   S   S   R   H   G   I   Q   K   K   L   K   R   V -

```
          TGGATCAGGTTCCTCAAAAGAAAGATGACTCAACTTGTAACTCCACGGTAGAGACAAGGG
     1021 ---------+---------+---------+---------+---------+---------+ 1080
          ACCTAGTCCAAGGAGTTTTCTTTCTACTGAGTTGAACATTGAGGTGCCATCTCTGTTCCC
``` a      W   I   R   F   L   K   R   K   M   T   Q   L   V   T   P   R   *   R   Q   G   -
b        G   S   G   S   S   K   E   R   *   L   N   L   *   L   H   G   R   D   K   G   -
c           D   Q   V   P   Q   K   K   D   D   S   T   C   N   S   T   V   E   T   R   A -

FIG. 4C

```
        CCCAAAAGGCGAGAACTGAATGTGCCCGAAAGTCGAGATCAGAGGAGATCATTGATGGCA
   1081 ---------+---------+---------+---------+---------+---------+ 1140
        GGGTTTTCCGCTCTTGACTTACACGGGCTTTCAGCTCTAGTCTCCTCTAGTAACTACCGT a        P  K  R  R  E  L  N  V  P  E  S  R  D  Q  R  R  S  L  M  A   -
b         P  K  G  E  N  *  M  C  P  K  V  E  I  R  G  D  H  *  W  H  -
c           Q  K  A  R  T  E  C  A  R  K  S  R  S  E  E  I  I  D  G  T -

CTTCAGAAATGAATGAAGGAAAGAGGTCCCAGAAGACGCCTAGTACACCACGAAGGGTCA
   1141 ---------+---------+---------+---------+---------+---------+ 1200
        GAAGTCTTTACTTACTTCCTTTCTCCAGGGTCTTCTGCGGATCATGTGGTGCTTCCCAGT a        L  Q  K  *  M  K  E  R  G  P  R  R  R  L  V  H  H  E  G  S   -
b         F  R  N  E  *  R  K  E  V  P  E  D  A  *  Y  T  T  K  G  H  -
c           S  E  M  N  E  G  K  R  S  Q  K  T  P  S  T  P  R  R  V  T -

CACAAGGGGCAGCCTCACCTGGGCATGGCATCCAAGAGAAGCTCCAAGTGGTGGATAAGG
   1201 ---------+---------+---------+---------+---------+---------+ 1260
        GTGTTCCCCGTCGGAGTGGACCCGTACCGTAGGTTCTCTTCGAGGTTCACCACCTATTCC a        H  K  G  Q  P  H  L  G  M  A  S  K  R  S  S  K  W  W  I  R   -
b         T  R  G  S  L  T  W  A  W  H  P  R  E  A  P  S  G  G  *  G  -
c           Q  G  A  A  S  P  G  H  G  I  Q  E  K  L  Q  V  V  D  K  V -

TGACTCAAAGGAAAGACGACTCAACCTGGAACTCAGAGGTCATGATGAGGGTCCAAAAGG
   1261 ---------+---------+---------+---------+---------+---------+ 1320
        ACTGAGTTTCCTTTCTGCTGAGTTGGACCTTGAGTCTCCAGTACTACTCCCAGGTTTTCC a        *  L  K  G  K  T  T  Q  P  G  T  Q  R  S  *  *  G  S  K  R   -
b         D  S  K  E  R  R  L  N  L  E  L  R  G  H  D  E  G  P  K  G  -
c           T  Q  R  K  D  D  S  T  W  N  S  E  V  M  M  R  V  Q  K  A -

CAAGAACTAAATGTGCCCGAAAGTCCAGATCGAAAGAAAAGAAAAAGGAGAAAGATATCT
   1321 ---------+---------+---------+---------+---------+---------+ 1380
        GTTCTTGATTTACACGGGCTTTCAGGTCTAGCTTTCTTTTCTTTTTCCTCTTTCTATAGA a        Q  E  L  N  V  P  E  S  P  D  R  K  K  R  K  R  R  K  I  S   -
b         K  N  *  M  C  P  K  V  Q  I  E  R  K  E  K  G  E  R  Y  L  -
c           R  T  K  C  A  R  K  S  R  S  K  E  K  K  K  E  K  D  I  C -

GTTCAAGCTCAAAAAGGAGATTTCAGAAAAATATTCACCGAAGAGGAAAACCCAAAAGTG
   1381 ---------+---------+---------+---------+---------+---------+ 1440
        CAAGTTCGAGTTTTTCCTCTAAAGTCTTTTTATAAGTGGCTTCTCCTTTTGGGTTTTCAC a        V  Q  A  Q  K  G  D  F  R  K  I  F  T  E  E  E  N  P  K  V   -
b         F  K  L  K  K  E  I  S  E  K  Y  S  P  K  R  K  T  Q  K  *  -
c           S  S  S  K  R  R  F  Q  K  N  I  H  R  R  G  K  P  K  S  D -
```

FIG. 4D

```
            ACACTGTGGATTTTCACTGTTCTAAGCTCCCCGTGACCTGTGGTGAGGCGAAAGGGATTT
      1441  ------------+---------+---------+---------+---------+---------+ 1500
            TGTGACACCTAAAAGTGACAAGATTCGAGGGGCACTGGACACCACTCCGCTTTCCCTAAA a         T  L  W  I  F  T  V  L  S  S  P  *  P  V  V  R  R  K  G  F  -
  b          H  C  G  F  S  L  F  *  A  P  R  D  L  W  *  G  E  R  D  F -
  c           T  V  D  F  H  C  S  K  L  P  V  T  C  G  E  A  K  G  I  L -

TATATAAGAAGAAAATGAAACACGGATCCTCAGTGAAGTGCATTCGGAATGAGGATGGAA
      1501  ------------+---------+---------+---------+---------+---------+ 1560
            ATATATTCTTCTTTTACTTTGTGCCTAGGAGTCACTTCACGTAAGCCTTACTCCTACCTT a         Y  I  R  R  K  *  N  T  D  P  Q  *  S  A  F  G  M  R  M  E  -
  b          I  *  E  E  N  E  T  R  I  L  S  E  V  H  S  E  *  G  W  N -
  c           Y  K  K  K  M  K  H  G  S  S  V  K  C  I  R  N  E  D  G  T -

CTTGGTTAACACCAAATGAATTTGAAGTCGAAGGAAAAGGAAGGAACGCAAAGAACTGGA
      1561  ------------+---------+---------+---------+---------+---------+ 1620
            GAACCAATTGTGGTTTACTTAAACTTCAGCTTCCTTTTCCTTCCTTGCGTTTCTTGACCT a         L  G  *  H  Q  M  N  L  K  S  K  E  K  E  G  T  Q  R  T  G  -
  b          L  V  N  T  K  *  I  *  S  R  R  K  R  K  E  R  K  E  L  E -
  c           W  L  T  P  N  E  F  E  V  E  G  K  G  R  N  A  K  N  W  K -

AACGGAATATACGTTGTGAAGGAAcGACCCTAGGAGAGCTGCTGAAGagtggactttgct
      1621  ------------+---------+---------+---------+---------+---------+ 1680
            TTGCCTTATATGCAACACTTCCTTgCTGGGATCCTCTCGACGACTTCtcacctgaaacga a         N  G  I  Y  V  V  K  E  R  P  *  E  S  C  *  R  V  D  F  A  -
  b          T  E  Y  T  L  *  R  N  D  P  R  R  A  A  E  E  W  T  L  L -
  c           R  N  I  R  C  E  G  T  T  L  G  E  L  L  K  S  G  L  C  S - ctgtcctccaagaataaatctcaagagagagttaaatagcaagtgaatttctactaccct
      1681  ------------+---------+---------+---------+---------+---------+ 1740
            gacaggaggttcttatttagagttctctctcaatttatcgttcacttaaagatgatggga a         L  S  S  K  N  K  S  Q  E  R  V  K  *  Q  V  N  F  Y  Y  P  -
  b          C  P  P  R  I  N  L  K  R  E  L  N  S  K  *  I  S  T  T  L -
  c           V  L  Q  E  *  I  S  R  E  S  *  I  A  S  E  F  L  L  P  S - ctcagtcaccatgttgcagactttccctgtctggaggctcaccttagagcttctgagttt
      1741  ------------+---------+---------+---------+---------+---------+ 1800
            gagtcagtggtacaacgtctgaaagggacagacctccgagtggaatctcgaagactcaaa a         L  S  H  H  V  A  D  F  P  C  L  E  A  H  L  R  A  S  E  F  -
  b          S  V  T  M  L  Q  T  F  P  V  W  R  L  T  L  E  L  L  S  F -
  c           Q  S  P  C  C  R  L  S  L  S  G  G  S  P  *  S  F  *  V  S -
```

FIG. 4E

```
            ccaagctctgagtcacctccacatttgggcatggcatcttcaaaacaattaatttgcata
    1801    ---------+---------+---------+---------+---------+---------+ 1860
            ggttcgagactcagtggaggtgtaaacccgtaccgtagaagttttgttaattaaacgtat a           P  S  S  E  S  P  P  H  L  G  M  A  S  S  K  Q  L  I  C  I   -
b            Q  A  L  S  H  L  H  I  W  A  W  H  L  Q  N  N  *  F  A  *  -
c             K  L  *  V  T  S  T  F  G  H  G  I  F  K  T  I  N  L  H  S -
            gttaatttgggatggggaagcaaatgactctaaaataaaaattaaatgaaaaagcgccg
    1861    ---------+---------+---------+---------+---------+--------- 1919
            caattaaaccctaccccttcgtttactgagattttatttttaatttacttttttcgcggc a           V  N  L  G  W  G  S  K  *  L  *  N  K  N  *  M  K  K  R     -
b            L  I  W  D  G  E  A  N  D  S  K  I  K  I  K  *  K  S  A    -
c             *  F  G  M  G  K  Q  M  T  L  K  *  K  L  N  E  K  A  P   -
a.: END
```

FIG. 4F

SEQUENCE LISTING

<160> NUMBER OF SEQ ID NOS: 15

<210> SEQ ID NO 1
<211> LENGTH: 2336
<212> TYPE: DNA
<213> ORGANISM: Homo sapiens

<400> SEQUENCE: 1

| | | | | | |
|---|---|---|---|---|---|
| tgtaactctc | ccaatcttga | ggagtgatcc | ctgtcccagc | ccctggaaag | cgaggaacga | 60 |
| caaactcaaa | gtccaggatg | ttcaccatga | caagagccat | ggaagaggct | cttttcagc | 120 |
| acttcatgca | ccagaagctg | gggatcgcct | atgccataca | caagccattt | cccttctttg | 180 |
| aaggcctcct | agacaactcc | atcatcacta | agagaatgta | catggaatct | ctggaagcct | 240 |
| gtagaaattt | gatccctgta | tccagagtgg | tgcacaacat | tctcacccaa | ctggagagga | 300 |
| cttttaacct | gtctcttctg | gtgacattgt | tcagtcaaat | taacctgcgt | gaatatccca | 360 |
| atctggtgac | gatttacaga | agcttcaaac | gtgttggtgc | ttcctatgaa | cggcagagca | 420 |
| gagacacacc | aatcctactt | gaagcccaa | ctggcctagc | agaaggaagc | tccctccata | 480 |
| ccccactggc | gctgccccac | acaaaccccc | tcaaccaag | ctgttcaccc | tgtgcgccaa | 540 |
| gagtcagtga | gcctggaaca | tcctcccagc | aaagcactga | gatcctgagt | gagtcgccca | 600 |
| gcccatctga | ccctgtcctg | cctctccctg | cactcatcca | ggaaggaaga | agcacttcag | 660 |
| tgaccaatga | caagttaaca | tccaaaatga | atgcggaaga | agactcagaa | gagatgccca | 720 |
| gcctcctcac | tagcactgtg | caagtggcca | gtgacaacct | gatcccccaa | ataagagata | 780 |
| aagaagaccc | tcaagagatg | ccccactctc | ccttgggctc | tatgccagag | ataagagata | 840 |
| attctccaga | accaaatgac | ccagaagagc | cccaggaggt | gtccagcaca | ccttcagaca | 900 |
| agaaaggaaa | gaaagaaaaa | agatgtatct | ggtcaactcc | aaaaggaga | cataagaaaa | 960 |
| aaagcctccc | aagagggaca | gcctcatcta | gacacggaat | ccaaagaag | ctcaaaaggg | 1020 |
| tggatcaggt | tcctcaaaag | aaagatgact | caacttgtaa | ctccacggta | gagacaaggg | 1080 |
| cccaaaaggc | gagaactgaa | tgtgcccgaa | agtcgagatc | agaggagatc | attgatggca | 1140 |
| cttcagaaat | gaatgaagga | aagaggtccc | agaagacgcc | tagtacacca | cgaagggtca | 1200 |
| cacaagggc | agcctcacct | gggcatggca | tccaagagaa | gctccaagtg | gtggataagg | 1260 |
| tgactcaaag | gaaagacgac | tcaacctgga | actcagaggt | catgatgagg | gtccaaaagg | 1320 |
| caagaactaa | atgtgcccga | aagtccagat | cgaaagaaaa | gaaaaggag | aaagatatct | 1380 |
| gttcaagctc | aaaaggaga | tttcagaaaa | atattcaccg | aagaggaaaa | cccaaaagtg | 1440 |
| acactgtgga | ttttcactgt | tctaagctcc | ccgtgacctg | tggtgaggcg | aaagggattt | 1500 |
| tatataagaa | gaaaatgaaa | cacggatcct | cagtgaagtg | cattcggaat | gaggatggaa | 1560 |
| cttggttaac | accaaatgaa | tttgaagtcg | aaggaaaagg | aaggaacgca | agaactggaa | 1620 |
| aacggaatat | acgttgtgaa | ggaacgaccc | taggagagct | gctgaagcgg | aaaaactcgg | 1680 |
| atgaatgcga | ggtgtgctgt | caaggggac | aacttctctg | ctgcggtact | tgtccacgag | 1740 |
| tcttccatga | ggactgtcac | atcccccctg | tggaagccaa | gaggatgctg | tggagttgca | 1800 |
| ccttctgcag | gatgaagagg | tcttcaggaa | gccaacagtg | ccatcatgta | tctaagaccc | 1860 |
| tggagaggca | gatgcagcct | caggaccagc | tgattcgaga | ttacggtgag | cccttcagg | 1920 |
| aagcaatgtg | gttggacctg | gttaaggaaa | ggctgattac | ggaaatgtac | acggtggcat | 1980 |
| ggtttgtgcg | agacatgcgc | ctgatgtttc | gcaaccataa | aacatttac | aaggcttctg | 2040 |

```
actttggcca ggtaggactt gacttagagg cagaatttga aaaagatctc aaagacgtgc    2100
tcggttttca tgaagccaat gacggcggtt tctggactct tccttgaccc tgttctgtaa    2160
agactgaagc atccccgacc tcaggattca gctgatggga ccctggcttg gactgttgat    2220
tgccagtgag tctgggatgt aattggctgc cctcaggacc caaacccaga cacttcatag    2280
gattatcaca ccctccatct ttattctttc tttttacctt taaaagtcta tatcta         2336
```

<210> SEQ ID NO 2
<211> LENGTH: 689
<212> TYPE: PRT
<213> ORGANISM: Homo sapiens

<400> SEQUENCE: 2

```
Met Phe Thr Met Thr Arg Ala Met Glu Glu Ala Leu Phe Gln His Phe
 1               5                  10                  15

Met His Gln Lys Leu Gly Ile Ala Tyr Ala Ile His Lys Pro Phe Pro
            20                  25                  30

Phe Phe Glu Gly Leu Leu Asp Asn Ser Ile Ile Thr Lys Arg Met Tyr
        35                  40                  45

Met Glu Ser Leu Glu Ala Cys Arg Asn Leu Ile Pro Val Ser Arg Val
    50                  55                  60

Val His Asn Ile Leu Thr Gln Leu Glu Arg Thr Phe Asn Leu Ser Leu
65                  70                  75                  80

Leu Val Thr Leu Phe Ser Gln Ile Asn Leu Arg Glu Tyr Pro Asn Leu
                85                  90                  95

Val Thr Ile Tyr Arg Ser Phe Lys Arg Val Gly Ala Ser Tyr Glu Arg
            100                 105                 110

Gln Ser Arg Asp Thr Pro Ile Leu Leu Glu Ala Pro Thr Gly Leu Ala
        115                 120                 125

Glu Gly Ser Ser Leu His Thr Pro Leu Ala Leu Pro His His Lys Pro
    130                 135                 140

Pro Gln Pro Ser Cys Ser Pro Cys Ala Pro Arg Val Ser Glu Pro Gly
145                 150                 155                 160

Thr Ser Ser Gln Gln Ser Thr Glu Ile Leu Ser Glu Ser Pro Ser Pro
                165                 170                 175

Ser Asp Pro Val Leu Pro Leu Pro Ala Leu Ile Gln Glu Gly Arg Ser
            180                 185                 190

Thr Ser Val Thr Asn Asp Lys Leu Thr Ser Lys Met Asn Ala Glu Glu
        195                 200                 205

Asp Ser Glu Glu Met Pro Ser Leu Leu Thr Ser Thr Val Gln Val Ala
    210                 215                 220

Ser Asp Asn Leu Ile Pro Gln Ile Arg Asp Lys Glu Asp Pro Gln Glu
225                 230                 235                 240

Met Pro His Ser Pro Leu Gly Ser Met Pro Glu Ile Arg Asp Asn Ser
                245                 250                 255

Pro Glu Pro Asn Asp Pro Glu Glu Pro Gln Glu Val Ser Ser Thr Pro
            260                 265                 270

Ser Asp Lys Lys Gly Lys Lys Arg Lys Arg Cys Ile Trp Ser Thr Pro
        275                 280                 285

Lys Arg Arg His Lys Lys Ser Leu Pro Arg Gly Thr Ala Ser Ser
    290                 295                 300

Arg His Gly Ile Gln Lys Lys Leu Lys Arg Val Asp Gln Val Pro Gln
305                 310                 315                 320
```

```
Lys Lys Asp Asp Ser Thr Cys Asn Ser Thr Val Glu Thr Arg Ala Gln
            325                 330                 335
Lys Ala Arg Thr Glu Cys Ala Arg Lys Ser Arg Ser Glu Glu Ile Ile
            340                 345                 350
Asp Gly Thr Ser Glu Met Asn Glu Gly Lys Arg Ser Gln Lys Thr Pro
            355                 360                 365
Ser Thr Pro Arg Arg Val Thr Gln Gly Ala Ala Ser Pro Gly His Gly
            370                 375                 380
Ile Gln Glu Lys Leu Gln Val Val Asp Lys Val Thr Gln Arg Lys Asp
385                 390                 395                 400
Asp Ser Thr Trp Asn Ser Glu Val Met Met Arg Val Gln Lys Ala Arg
                405                 410                 415
Thr Lys Cys Ala Arg Lys Ser Arg Ser Lys Glu Lys Lys Glu Lys
            420                 425                 430
Asp Ile Cys Ser Ser Lys Arg Arg Phe Gln Lys Asn Ile His Arg
            435                 440                 445
Arg Gly Lys Pro Lys Ser Asp Thr Val Asp Phe His Cys Ser Lys Leu
            450                 455                 460
Pro Val Thr Cys Gly Glu Ala Lys Gly Ile Leu Tyr Lys Lys Lys Met
465                 470                 475                 480
Lys His Gly Ser Ser Val Lys Cys Ile Arg Asn Glu Asp Gly Thr Trp
                485                 490                 495
Leu Thr Pro Asn Glu Phe Glu Val Glu Gly Lys Gly Arg Asn Ala Lys
                500                 505                 510
Asn Trp Lys Arg Asn Ile Arg Cys Glu Gly Thr Thr Leu Gly Glu Leu
            515                 520                 525
Leu Lys Arg Lys Asn Ser Asp Glu Cys Glu Val Cys Cys Gln Gly Gly
            530                 535                 540
Gln Leu Leu Cys Cys Gly Thr Cys Pro Arg Val Phe His Glu Asp Cys
545                 550                 555                 560
His Ile Pro Pro Val Glu Ala Lys Arg Met Leu Trp Ser Cys Thr Phe
                565                 570                 575
Cys Arg Met Lys Arg Ser Ser Gly Ser Gln Gln Cys His His Val Ser
                580                 585                 590
Lys Thr Leu Glu Arg Gln Met Gln Pro Gln Asp Gln Leu Ile Arg Asp
            595                 600                 605
Tyr Gly Glu Pro Phe Gln Glu Ala Met Trp Leu Asp Leu Val Lys Glu
            610                 615                 620
Arg Leu Ile Thr Glu Met Tyr Thr Val Ala Trp Phe Val Arg Asp Met
625                 630                 635                 640
Arg Leu Met Phe Arg Asn His Lys Thr Phe Tyr Lys Ala Ser Asp Phe
                645                 650                 655
Gly Gln Val Gly Leu Asp Leu Glu Ala Glu Phe Glu Lys Asp Leu Lys
            660                 665                 670
Asp Val Leu Gly Phe His Glu Ala Asn Asp Gly Gly Phe Trp Thr Leu
            675                 680                 685
Pro

<210> SEQ ID NO 3
<211> LENGTH: 753
<212> TYPE: PRT
<213> ORGANISM: Homo sapiens

<400> SEQUENCE: 3
```

-continued

```
Met Ala Gln Gly Gln Gln Gly Gln Met Ala Ser Gly Asp Ser Asn
 1               5                  10                 15

Leu Asn Phe Arg Met Val Ala Glu Ile Gln Asn Val Glu Gly Gln Asn
             20                  25                 30

Leu Gln Glu Gln Val Cys Pro Glu Pro Ile Phe Arg Phe Phe Arg Glu
             35                  40                  45

Asn Lys Val Glu Ile Ala Ser Ala Ile Thr Arg Pro Phe Pro Phe Leu
         50                  55                  60

Met Gly Leu Arg Asp Arg Ser Phe Ile Ser Glu Gln Met Tyr Glu His
65                   70                  75                  80

Phe Gln Glu Ala Phe Arg Asn Leu Val Pro Val Thr Arg Val Met Tyr
                 85                  90                  95

Cys Val Leu Ser Glu Leu Glu Lys Thr Phe Gly Trp Ser His Leu Glu
             100                 105                 110

Ala Leu Phe Ser Arg Ile Asn Leu Met Ala Tyr Pro Asp Leu Asn Glu
             115                 120                 125

Ile Tyr Arg Ser Phe Gln Asn Val Cys Tyr Glu His Ser Pro Leu Gln
         130                 135                 140

Met Asn Asn Val Asn Asp Leu Glu Asp Arg Pro Arg Leu Leu Pro Tyr
145                 150                 155                 160

Gly Lys Gln Glu Asn Ser Asn Ala Cys His Glu Met Asp Asp Ile Ala
                 165                 170                 175

Val Pro Gln Glu Ala Leu Ser Ser Pro Arg Cys Glu Pro Gly Phe
             180                 185                 190

Ser Ser Glu Ser Cys Glu Gln Leu Ala Leu Pro Lys Ala Gly Gly Gly
         195                 200                 205

Asp Ala Glu Asp Ala Pro Ser Leu Leu Pro Val Ser Cys Lys Leu Ala
210                 215                 220

Ile Gln Ile Asp Glu Gly Glu Ser Glu Met Pro Lys Leu Leu Pro
225                 230                 235                 240

Tyr Asp Thr Glu Glu Thr Phe Asp Leu Lys Thr Pro Gln Val Thr Asn
             245                 250                 255

Glu Gly Glu Pro Glu Lys Gly Leu Cys Leu Leu Pro Gly Glu Gly Glu
             260                 265                 270

Glu Gly Ser Asp Asp Cys Ser Glu Met Cys Asp Gly Glu Glu Arg Gln
             275                 280                 285

Glu Ala Ser Ser Ser Leu Ala Arg Arg Gly Ser Val Ser Ser Glu Leu
         290                 295                 300

Glu Asn His Pro Met Asn Glu Glu Gly Glu Ser Glu Glu Leu Ala Ser
305                 310                 315                 320

Ser Leu Leu Tyr Asp Asn Val Pro Gly Ala Glu Gln Ser Ala Tyr Glu
             325                 330                 335

Asn Glu Lys Cys Ser Cys Val Met Cys Phe Ser Glu Glu Val Pro Gly
             340                 345                 350

Ser Pro Glu Ala Arg Thr Glu Ser Asp Gln Ala Cys Gly Thr Met Asp
             355                 360                 365

Thr Val Asp Ile Ala Asn Asn Ser Thr Leu Gly Lys Pro Lys Arg Lys
         370                 375                 380

Arg Arg Lys Lys Arg Gly His Gly Trp Ser Arg Met Arg Met Arg Arg
385                 390                 395                 400

Gln Lys Asn Ser Gln Gln Asn Asp Asn Ser Lys Ala Asp Gly Gln Val
                 405                 410                 415

Val Ser Ser Glu Lys Lys Ala Asn Val Asn Leu Lys Asp Leu Ser Lys
```

-continued

```
                    420                 425                 430
Ile Arg Gly Arg Lys Arg Gly Lys Pro Gly Thr Arg Phe Thr Gln Ser
            435                 440                 445
Asp Arg Ala Ala Gln Lys Arg Val Arg Ser Arg Ala Ser Arg Lys His
        450                 455                 460
Lys Asp Glu Thr Val Asp Phe Lys Ala Pro Leu Leu Pro Val Thr Cys
465                 470                 475                 480
Gly Gly Val Lys Gly Ile Leu His Lys Lys Lys Leu Gln Gln Gly Ile
                485                 490                 495
Leu Val Lys Cys Ile Gln Thr Glu Asp Gly Lys Trp Phe Thr Pro Thr
            500                 505                 510
Glu Phe Glu Ile Lys Gly Gly His Ala Arg Ser Lys Asn Trp Arg Leu
        515                 520                 525
Ser Val Arg Cys Gly Gly Trp Pro Leu Arg Trp Leu Met Glu Asn Gly
        530                 535                 540
Phe Leu Pro Asp Pro Pro Arg Ile Arg Tyr Arg Lys Lys Lys Arg Ile
545                 550                 555                 560
Leu Lys Ser Gln Asn Asn Ser Ser Val Asp Pro Cys Met Arg Asn Leu
                565                 570                 575
Asp Glu Cys Glu Val Cys Arg Asp Gly Gly Glu Leu Phe Cys Cys Asp
            580                 585                 590
Thr Cys Ser Arg Val Phe His Glu Asp Cys His Ile Pro Pro Val Glu
        595                 600                 605
Ala Glu Arg Thr Pro Trp Asn Cys Ile Phe Cys Arg Met Lys Glu Ser
        610                 615                 620
Pro Gly Ser Gln Gln Cys Cys Gln Glu Ser Glu Val Leu Glu Arg Gln
625                 630                 635                 640
Met Cys Pro Glu Glu Gln Leu Lys Cys Glu Phe Leu Leu Leu Lys Val
                645                 650                 655
Tyr Cys Cys Ser Glu Ser Ser Phe Phe Ala Lys Ile Pro Tyr Tyr Tyr
            660                 665                 670
Tyr Ile Arg Glu Ala Cys Gln Gly Leu Lys Glu Pro Met Trp Leu Asp
        675                 680                 685
Lys Ile Lys Lys Arg Leu Asn Glu His Gly Tyr Pro Gln Val Glu Gly
        690                 695                 700
Phe Val Gln Asp Met Arg Leu Ile Phe Gln Asn His Arg Ala Ser Tyr
705                 710                 715                 720
Lys Tyr Lys Asp Phe Gly Gln Met Gly Phe Arg Leu Glu Ala Glu Phe
                725                 730                 735
Glu Lys Asn Phe Lys Glu Val Phe Ala Ile Gln Glu Thr Asn Gly Asn
            740                 745                 750
Asn
```

```
<210> SEQ ID NO 4
<211> LENGTH: 1919
<212> TYPE: DNA
<213> ORGANISM: Homo sapiens

<400> SEQUENCE: 4
tgtaactctc ccaatcttga ggagtgatcc ctgtcccagc ccctggaaag cgaggaacga      60
caaactcaaa gtccaggatg ttcaccatga caagagccat ggaagaggct cttttcagc     120 acttcatgca ccagaagctg gggatcgcct atgccataca caagccattt cccttctttg    180
aaggcctcct agacaactcc atcatcacta agagaatgta catggaatct ctggaagcct    240
```

-continued

```
gtagaaattt gatccctgta tccagagtgg tgcacaacat tctcacccaa ctggagagga    300
cttttaacct gtctcttctg gtgacattgt tcagtcaaat taacctgcgt gaatatccca    360
atctggtgac gatttacaga agcttcaaac gtgttggtgc ttcctatgaa cggcagagca    420
gagacacacc aatcctactt gaagcoccaa ctggcctagc agaaggaagc tccctccata    480
ccccactggc gctgccccac cacaaacccc ctcaaccaag ctgttcaccc tgtgcgccaa    540
gagtcagtga gcctggaaca tcctcccagc aaagcactga gatcctgagt gagtcgccca    600
gcccatctga ccctgtcctg cctctccctg cactcatcca ggaaggaaga agcacttcag    660
tgaccaatga caagttaaca tccaaaatga atgcggaaga agactcagaa gagatgccca    720
gcctcctcac tagcactgtg caagtggcca gtgacaacct gatcccccaa ataagagata    780
aagaagaccc tcaagagatg ccccactctc ccttgggctc tatgccagag ataagagata    840
attctccaga accaaatgac ccagaagagc cccaggaggt gtccagcaca ccttcagaca    900
agaaaggaaa gaaaagaaaa agatgtatct ggtcaactcc aaaaaggaga cataagaaaa    960
aaagcctccc aagagggaca gcctcatcta gacacggaat ccaaaagaag ctcaaaaggg   1020
tggatcaggt tcctcaaaag aaagatgact caacttgtaa ctccacggta gagacaaggg   1080
cccaaaaggc gagaactgaa tgtgcccgaa agtcgagatc agaggagatc attgatggca   1140
cttcagaaat gaatgaagga agaggtccc agaagacgcc tagtacacca cgaagggtca   1200
cacaaggggc agcctcacct gggcatggca tccaagagaa gctccaagtg gtggataagg   1260
tgactcaaag gaaagacgac tcaacctgga actcagaggt catgatgagg gtccaaaagg   1320
caagaactaa atgtgcccga aagtccagat cgaaagaaaa gaaaaaggag aaagatatct   1380
gttcaagctc aaaaaggaga tttcagaaaa atattcaccg aagaggaaaa cccaaaagtg   1440
acactgtgga ttttcactgt tctaagctcc ccgtgacctg tggtgaggcg aaagggattt   1500
tatataagaa gaaaatgaaa cacggatcct cagtgaagtg cattcggaat gaggatggaa   1560
cttggttaac accaaatgaa tttgaagtcg aaggaaaagg aaggaacgca agaactggaa   1620
aacggaatat acgttgtgaa ggaacgaccc taggagagct gctgaagagt ggactttgct   1680
ctgtcctcca agaataaatc tcaagagaga gttaaatagc aagtgaattt ctactaccct   1740
ctcagtcacc atgttgcaga cttcctgt ctggaggctc accttagagc ttctgagttt   1800
ccaagctctg agtcacctcc acatttgggc atggcatctt caaaacaatt aatttgcata   1860
gttaatttgg gatggggaag caaatgactc taaaataaaa attaaatgaa aaagcgccg    1919
```

<210> SEQ ID NO 5
<211> LENGTH: 630
<212> TYPE: PRT
<213> ORGANISM: Homo sapiens

<400> SEQUENCE: 5

```
Leu Ser Gln Ser Gly Val Ile Pro Val Pro Ala Pro Gly Lys Arg Gly
 1               5                  10                  15

Thr Thr Asn Ser Lys Ser Arg Met Phe Thr Met Thr Arg Ala Met Glu
             20                  25                  30

Glu Ala Leu Phe Gln His Phe Met His Gln Lys Leu Gly Ile Ala Tyr
         35                  40                  45

Ala Ile His Lys Pro Phe Pro Phe Glu Gly Leu Leu Asp Asn Ser
     50                  55                  60

Ile Ile Thr Lys Arg Met Tyr Met Glu Ser Leu Glu Ala Cys Arg Asn
65                  70                  75                  80
```

-continued

```
Leu Ile Pro Val Ser Arg Val Val His Asn Ile Leu Thr Gln Leu Glu
                85                  90                  95

Arg Thr Phe Asn Leu Ser Leu Leu Val Thr Leu Phe Ser Gln Ile Asn
            100                 105                 110

Leu Arg Glu Tyr Pro Asn Leu Val Thr Ile Tyr Arg Ser Phe Lys Arg
        115                 120                 125

Val Gly Ala Ser Tyr Glu Arg Gln Ser Arg Asp Thr Pro Ile Leu Leu
    130                 135                 140

Glu Ala Pro Thr Gly Leu Ala Glu Gly Ser Ser Leu His Thr Pro Leu
145                 150                 155                 160

Ala Leu Pro His His Lys Pro Pro Gln Pro Ser Cys Ser Pro Cys Ala
                165                 170                 175

Pro Arg Val Ser Glu Pro Gly Thr Ser Ser Gln Gln Ser Thr Glu Ile
            180                 185                 190

Leu Ser Glu Ser Pro Ser Pro Ser Asp Pro Val Leu Pro Leu Pro Ala
        195                 200                 205

Leu Ile Gln Glu Gly Arg Ser Thr Ser Val Thr Asn Asp Lys Leu Thr
    210                 215                 220

Ser Lys Met Asn Ala Glu Glu Asp Ser Glu Glu Met Pro Ser Leu Leu
225                 230                 235                 240

Thr Ser Thr Val Gln Val Ala Ser Asp Asn Leu Ile Pro Gln Ile Arg
                245                 250                 255

Asp Lys Glu Asp Pro Gln Glu Met Pro His Ser Pro Leu Gly Ser Met
            260                 265                 270

Pro Glu Ile Arg Asp Asn Ser Pro Glu Pro Asn Asp Pro Glu Glu Pro
        275                 280                 285

Gln Glu Val Ser Ser Thr Pro Ser Asp Lys Lys Gly Lys Lys Arg Lys
    290                 295                 300

Arg Cys Ile Trp Ser Thr Pro Lys Arg His Lys Lys Lys Ser Leu
305                 310                 315                 320

Pro Arg Gly Thr Ala Ser Ser Arg His Gly Ile Gln Lys Lys Leu Lys
                325                 330                 335

Arg Val Asp Gln Val Pro Gln Lys Lys Asp Asp Ser Thr Cys Asn Ser
            340                 345                 350

Thr Val Glu Thr Arg Ala Gln Lys Ala Arg Thr Glu Cys Ala Arg Lys
        355                 360                 365

Ser Arg Ser Glu Glu Ile Ile Asp Gly Thr Ser Glu Met Asn Glu Gly
    370                 375                 380

Lys Arg Ser Gln Lys Thr Pro Ser Thr Pro Arg Arg Val Thr Gln Gly
385                 390                 395                 400

Ala Ala Ser Pro Gly His Gly Ile Gln Glu Lys Leu Gln Val Val Asp
                405                 410                 415

Lys Val Thr Gln Arg Lys Asp Asp Ser Thr Trp Asn Ser Glu Val Met
            420                 425                 430

Met Arg Val Gln Lys Ala Arg Thr Lys Cys Ala Arg Lys Ser Arg Ser
        435                 440                 445

Lys Glu Lys Lys Lys Glu Lys Asp Ile Cys Ser Ser Ser Lys Arg Arg
    450                 455                 460

Phe Gln Lys Asn Ile His Arg Arg Gly Lys Pro Lys Ser Asp Thr Val
465                 470                 475                 480

Asp Phe His Cys Ser Lys Leu Pro Val Thr Cys Gly Glu Ala Lys Gly
                485                 490                 495
```

```
Ile Leu Tyr Lys Lys Lys Met Lys His Gly Ser Ser Val Lys Cys Ile
            500                 505                 510

Arg Asn Glu Asp Gly Thr Trp Leu Thr Pro Asn Glu Phe Glu Val Glu
        515                 520                 525

Gly Lys Gly Arg Asn Ala Lys Asn Trp Lys Arg Asn Ile Arg Cys Glu
    530                 535                 540

Gly Thr Thr Leu Gly Glu Leu Leu Lys Ser Gly Leu Cys Ser Val Leu
545                 550                 555                 560

Gln Glu Ile Ser Arg Glu Ser Ile Ala Ser Glu Phe Leu Leu Pro Ser
                565                 570                 575

Gln Ser Pro Cys Cys Arg Leu Ser Leu Ser Gly Ser Pro Ser Phe
            580                 585                 590

Val Ser Lys Leu Val Thr Ser Thr Phe Gly His Gly Ile Phe Lys Thr
        595                 600                 605

Ile Asn Leu His Ser Phe Gly Met Gly Lys Gln Met Thr Leu Lys Lys
    610                 615                 620

Leu Asn Glu Lys Ala Pro
625                 630

<210> SEQ ID NO 6
<211> LENGTH: 744
<212> TYPE: PRT
<213> ORGANISM: Homo sapiens

<400> SEQUENCE: 6

Cys Asn Ser Pro Asn Leu Glu Glu Ser Leu Ser Gln Pro Leu Glu Ser
1               5                   10                  15

Glu Glu Arg Gln Thr Gln Ser Pro Gly Cys Ser Pro Gln Glu Pro Trp
            20                  25                  30

Lys Arg Leu Phe Phe Ser Thr Ser Cys Thr Arg Ser Trp Gly Ser Pro
        35                  40                  45

Met Pro Tyr Thr Ser His Phe Pro Ser Leu Lys Ala Ser Thr Thr Pro
    50                  55                  60

Ser Ser Leu Arg Glu Cys Thr Trp Asn Leu Trp Lys Pro Val Glu Ile
65                  70                  75                  80

Ser Leu Tyr Pro Glu Trp Cys Thr Thr Phe Ser Pro Asn Trp Arg Gly
                85                  90                  95

Leu Leu Thr Cys Leu Phe Trp His Cys Ser Val Lys Leu Thr Cys Val
            100                 105                 110

Asn Ile Pro Ile Trp Arg Phe Thr Glu Ala Ser Asn Val Leu Val Leu
        115                 120                 125

Pro Met Asn Gly Arg Ala Glu Thr His Gln Ser Tyr Leu Lys Pro Gln
    130                 135                 140

Leu Ala Gln Lys Glu Ala Pro Ser Ile Pro His Trp Arg Cys Pro Thr
145                 150                 155                 160

Thr Asn Pro Leu Asn Gln Ala Val His Pro Val Arg Gln Glu Ser Val
                165                 170                 175

Ser Leu Glu His Pro Pro Ser Lys Ala Leu Arg Ser Val Ser Arg Pro
            180                 185                 190

Ala His Leu Thr Leu Ser Cys Leu Ser Leu His Ser Ser Arg Lys Glu
        195                 200                 205

Glu Ala Leu Gln Pro Met Thr Ser His Pro Lys Met Arg Lys Lys Thr
    210                 215                 220

Gln Lys Arg Cys Pro Ala Ser Ser Leu Ala Leu Cys Lys Trp Pro Val
225                 230                 235                 240
```

```
Thr Thr Ser Pro Lys Glu Ile Lys Lys Thr Leu Lys Arg Cys Pro Thr
            245                 250                 255
Leu Pro Trp Ala Leu Cys Gln Arg Glu Ile Ile Leu Gln Asn Gln Met
            260                 265                 270
Thr Gln Lys Ser Pro Arg Arg Cys Pro Ala His Leu Gln Thr Arg Lys
            275                 280                 285
Glu Arg Lys Glu Lys Asp Val Ser Gly Gln Leu Gln Lys Gly Asp Ile
            290                 295                 300
Arg Lys Lys Ala Ser Gln Glu Gly Gln Pro His Leu Asp Thr Glu Ser
305                 310                 315                 320
Lys Arg Ser Ser Lys Gly Trp Ile Arg Phe Leu Lys Arg Lys Met Thr
                325                 330                 335
Gln Leu Val Thr Pro Arg Arg Gln Gly Pro Lys Arg Arg Glu Leu Asn
                340                 345                 350
Val Pro Glu Ser Arg Asp Gln Arg Arg Ser Leu Met Ala Leu Gln Lys
                355                 360                 365
Met Lys Glu Arg Gly Pro Arg Arg Arg Leu Val His His Glu Gly Ser
            370                 375                 380
His Lys Gly Gln Pro His Leu Gly Met Ala Ser Lys Arg Ser Ser Lys
385                 390                 395                 400
Trp Trp Ile Arg Leu Lys Gly Lys Thr Thr Gln Pro Gly Thr Gln Arg
                405                 410                 415
Ser Gly Ser Lys Arg Gln Glu Leu Asn Val Pro Glu Ser Pro Asp Arg
                420                 425                 430
Lys Lys Arg Lys Arg Lys Ile Ser Val Gln Ala Gln Lys Gly Asp
                435                 440                 445
Phe Arg Lys Ile Phe Thr Glu Glu Asn Pro Lys Val Thr Leu Trp
            450                 455                 460
Ile Phe Thr Val Leu Ser Ser Pro Val Val Arg Arg Lys Gly Phe
465                 470                 475                 480
Tyr Ile Arg Arg Lys Asn Thr Asp Pro Gln Ser Ala Phe Gly Met Arg
                485                 490                 495
Met Glu Leu Gly His Gln Met Asn Leu Lys Ser Lys Glu Lys Glu Gly
            500                 505                 510
Thr Gln Arg Thr Gly Asn Gly Ile Tyr Val Val Lys Glu Arg Pro Glu
            515                 520                 525
Ser Cys Ser Gly Lys Thr Arg Met Asn Ala Arg Cys Ala Val Lys Gly
            530                 535                 540
Asp Asn Phe Ser Ala Ala Val Leu Val His Glu Ser Ser Met Arg Thr
545                 550                 555                 560
Val Thr Ser Pro Leu Trp Lys Pro Arg Gly Cys Cys Gly Val Ala Pro
                565                 570                 575
Ser Ala Gly Arg Gly Leu Gln Glu Ala Asn Ser Ala Ile Met Tyr Leu
                580                 585                 590
Arg Pro Trp Arg Gly Arg Cys Ser Leu Arg Thr Ser Phe Glu Ile Thr
            595                 600                 605
Val Ser Pro Phe Arg Lys Gln Cys Gly Trp Thr Trp Leu Arg Lys Gly
            610                 615                 620
Leu Arg Lys Cys Thr Arg Trp His Gly Leu Cys Glu Thr Cys Ala Cys
625                 630                 635                 640
Phe Ala Thr Ile Lys His Phe Thr Arg Leu Leu Thr Leu Ala Arg Asp
                645                 650                 655
```

-continued

```
Leu Thr Arg Gln Asn Leu Lys Lys Ile Ser Lys Thr Cys Ser Val Phe
            660                 665                 670

Met Lys Pro Met Thr Ala Val Ser Gly Leu Phe Leu Asp Pro Val Leu
        675                 680                 685

Arg Leu Lys His Pro Arg Pro Gln Asp Ser Ala Asp Gly Thr Leu Ala
    690                 695                 700

Trp Thr Val Asp Cys Gln Val Trp Asp Val Ile Gly Cys Pro Gln Asp
705                 710                 715                 720

Pro Asn Pro Asp Thr Ser Asp Tyr His Thr Leu His Leu Tyr Ser Phe
                725                 730                 735

Phe Leu Pro Leu Lys Val Tyr Ile
            740

<210> SEQ ID NO 7
<211> LENGTH: 728
<212> TYPE: PRT
<213> ORGANISM: Homo sapiens

<400> SEQUENCE: 7

Val Thr Leu Pro Ile Leu Arg Ser Asp Pro Cys Pro Ser Pro Trp Lys
1               5                   10                  15

Ala Arg Asn Asp Lys Leu Lys Val Gln Asp Val His His Asp Lys Ser
            20                  25                  30

His Gly Arg Gly Ser Phe Ser Ala Leu His Ala Pro Glu Ala Gly Asp
        35                  40                  45

Arg Leu Cys His Thr Gln Ala Ile Ser Leu Leu Arg Pro Pro Arg Gln
    50                  55                  60

Leu His His Glu Asn Val His Gly Ile Ser Gly Ser Leu Lys Phe
65                  70                  75                  80

Asp Pro Cys Ile Gln Ser Gly Ala Gln His Ser His Pro Thr Gly Glu
                85                  90                  95

Asp Phe Pro Val Ser Ser Gly Asp Ile Val Gln Ser Asn Pro Ala Ile
            100                 105                 110

Ser Gln Ser Gly Asp Asp Leu Gln Lys Leu Gln Thr Cys Trp Cys Phe
        115                 120                 125

Leu Thr Ala Glu Gln Arg His Thr Asn Pro Thr Ser Pro Asn Trp Pro
130                 135                 140

Ser Arg Arg Lys Leu Pro Pro Tyr Pro Thr Gly Ala Ala Pro Pro Gln
145                 150                 155                 160

Thr Pro Ser Thr Lys Leu Phe Thr Leu Cys Ala Lys Ser Gln Ala Trp
                165                 170                 175

Asn Ile Leu Pro Ala Lys His Asp Pro Glu Val Ala Gln Pro Ile Pro
            180                 185                 190

Cys Pro Ala Ser Pro Cys Thr His Pro Gly Arg Lys Lys His Phe Ser
        195                 200                 205

Asp Gln Gln Val Asn Ile Gln Asn Glu Cys Gly Arg Arg Leu Arg Arg
    210                 215                 220

Asp Ala Gln Pro Pro His His Cys Ala Ser Gly Gln Gln Pro Asp Pro
225                 230                 235                 240

Pro Asn Lys Arg Arg Pro Ser Arg Asp Ala Pro Leu Ser Leu Gly
                245                 250                 255

Leu Tyr Ala Arg Asp Lys Arg Phe Ser Arg Thr Lys Pro Arg Arg Ala
            260                 265                 270

Pro Gly Gly Val Gln His Thr Arg Phe Arg Gln Glu Arg Lys Glu Lys Lys
        275                 280                 285
```

```
Lys Met Tyr Leu Val Asn Ser Lys Lys Glu Thr Glu Lys Lys Pro Pro
    290                 295                 300

Lys Arg Asp Ser Leu Ile Thr Arg Asn Pro Lys Glu Ala Gln Lys Gly
305                 310                 315                 320

Gly Ser Gly Ser Ser Lys Glu Arg Leu Asn Leu Leu His Gly Arg Asp
                325                 330                 335

Lys Gly Pro Lys Gly Glu Asn Met Cys Pro Lys Val Glu Ile Arg Gly
            340                 345                 350

Asp His Trp His Phe Arg Asn Glu Arg Lys Glu Val Pro Glu Asp Ala
        355                 360                 365

Tyr Thr Thr Lys Gly His Thr Arg Gly Ser Leu Thr Trp Ala Trp His
    370                 375                 380

Pro Arg Glu Ala Pro Ser Gly Gly Gly Asp Ser Lys Glu Arg Arg Leu
385                 390                 395                 400

Asn Leu Glu Leu Arg Gly His Asp Glu Gly Pro Lys Gly Lys Asn Met
                405                 410                 415

Cys Pro Lys Val Gln Ile Glu Arg Lys Glu Lys Gly Glu Arg Tyr Leu
            420                 425                 430

Phe Lys Leu Lys Lys Glu Ile Ser Glu Lys Tyr Ser Pro Lys Arg Lys
        435                 440                 445

Thr Gln Lys His Cys Gly Phe Ser Leu Phe Ala Pro Arg Asp Leu Trp
    450                 455                 460

Gly Glu Arg Asp Phe Ile Glu Glu Asn Glu Thr Arg Ile Leu Ser Glu
465                 470                 475                 480

Val His Ser Glu Gly Trp Asn Leu Val Asn Thr Lys Ile Ser Arg Arg
                485                 490                 495

Lys Arg Lys Glu Arg Lys Glu Leu Glu Thr Glu Tyr Thr Leu Arg Asn
            500                 505                 510

Asp Pro Arg Arg Ala Ala Glu Ala Glu Lys Leu Gly Met Arg Gly Val
        515                 520                 525

Leu Ser Arg Gly Thr Thr Ser Leu Leu Arg Tyr Leu Ser Thr Ser Leu
    530                 535                 540

Pro Gly Leu Ser His Pro Pro Cys Gly Ser Gln Glu Asp Ala Val Glu
545                 550                 555                 560

Leu His Leu Leu Gln Asp Glu Glu Val Phe Arg Lys Pro Thr Val Pro
                565                 570                 575

Ser Cys Ile Asp Pro Gly Glu Ala Asp Ala Ala Ser Gly Pro Ala Asp
            580                 585                 590

Ser Arg Leu Arg Ala Leu Ser Gly Ser Asn Val Val Gly Pro Gly Gly
        595                 600                 605

Lys Ala Asp Tyr Gly Asn Val His Gly Gly Met Val Cys Ala Arg His
    610                 615                 620

Ala Pro Asp Val Ser Gln Pro Asn Ile Leu Gln Gly Phe Leu Trp Pro
625                 630                 635                 640

Gly Arg Thr Leu Arg Gly Arg Ile Lys Arg Ser Gln Arg Arg Ala Arg
                645                 650                 655

Phe Ser Ser Gln Arg Arg Phe Leu Asp Ser Ser Leu Thr Leu Phe Cys
            660                 665                 670

Lys Asp Ser Ile Pro Asp Leu Arg Ile Gln Leu Met Gly Pro Trp Leu
        675                 680                 685

Gly Leu Leu Ile Ala Ser Glu Ser Gly Met Leu Ala Ala Leu Arg Thr
    690                 695                 700
```

-continued

```
Gln Thr Gln Thr Leu His Arg Ile Ile Thr Pro Ser Ile Phe Ile Leu
705                 710                 715                 720

Ser Phe Tyr Leu Lys Ser Ile Ser
                725

<210> SEQ ID NO 8
<211> LENGTH: 610
<212> TYPE: PRT
<213> ORGANISM: Homo sapiens

<400> SEQUENCE: 8

Cys Asn Ser Pro Asn Leu Glu Glu Ser Leu Ser Gln Pro Leu Glu Ser
1               5                   10                  15

Glu Glu Arg Gln Thr Gln Ser Pro Gly Cys Ser Pro Gln Glu Pro Trp
            20                  25                  30

Lys Arg Leu Phe Phe Ser Thr Ser Cys Thr Arg Ser Trp Gly Ser Pro
        35                  40                  45

Met Pro Tyr Thr Ser His Phe Pro Ser Leu Lys Ala Ser Thr Thr Pro
    50                  55                  60

Ser Ser Leu Arg Glu Cys Thr Trp Asn Leu Trp Lys Pro Val Glu Ile
65                  70                  75                  80

Ser Leu Tyr Pro Glu Trp Cys Thr Thr Phe Ser Pro Asn Trp Arg Gly
                85                  90                  95

Leu Leu Thr Cys Leu Phe Trp His Cys Ser Val Lys Leu Thr Cys Val
            100                 105                 110

Asn Ile Pro Ile Trp Arg Phe Thr Glu Ala Ser Asn Val Leu Val Leu
        115                 120                 125

Pro Met Asn Gly Arg Ala Glu Thr His Gln Ser Tyr Leu Lys Pro Gln
    130                 135                 140

Leu Ala Gln Lys Glu Ala Pro Ser Ile Pro His Trp Arg Cys Pro Thr
145                 150                 155                 160

Thr Asn Pro Leu Asn Gln Ala Val His Pro Val Arg Gln Glu Ser Val
                165                 170                 175

Ser Leu Glu His Pro Pro Ser Lys Ala Leu Arg Ser Val Ser Arg Pro
            180                 185                 190

Ala His Leu Thr Leu Ser Cys Leu Ser Leu His Ser Ser Arg Lys Glu
        195                 200                 205

Glu Ala Leu Gln Pro Met Thr Ser His Pro Lys Met Arg Lys Lys Thr
    210                 215                 220

Gln Lys Arg Cys Pro Ala Ser Ser Leu Ala Leu Cys Lys Trp Pro Val
225                 230                 235                 240

Thr Thr Ser Pro Lys Glu Ile Lys Lys Thr Leu Lys Arg Cys Pro Thr
                245                 250                 255

Leu Pro Trp Ala Leu Cys Gln Arg Glu Ile Ile Leu Gln Asn Gln Met
            260                 265                 270

Thr Gln Lys Ser Pro Arg Arg Cys Pro Ala His Leu Gln Thr Arg Lys
        275                 280                 285

Glu Arg Lys Glu Lys Asp Val Ser Gly Gln Leu Gln Lys Gly Asp Ile
    290                 295                 300

Arg Lys Lys Ala Ser Gln Glu Gly Gln Pro His Leu Asp Thr Glu Ser
305                 310                 315                 320

Lys Arg Ser Ser Lys Gly Trp Ile Arg Phe Leu Lys Arg Lys Met Thr
                325                 330                 335

Gln Leu Val Thr Pro Arg Arg Gln Gly Pro Lys Arg Arg Glu Leu Asn
            340                 345                 350
```

```
Val Pro Glu Ser Arg Asp Gln Arg Arg Ser Leu Met Ala Leu Gln Lys
            355                 360                 365

Met Lys Glu Arg Gly Pro Arg Arg Leu Val His His Glu Gly Ser
    370                 375                 380

His Lys Gly Gln Pro His Leu Gly Met Ala Ser Lys Arg Ser Ser Lys
385                 390                 395                 400

Trp Trp Ile Arg Leu Lys Gly Lys Thr Thr Gln Pro Gly Thr Gln Arg
                405                 410                 415

Ser Gly Ser Lys Arg Gln Glu Leu Asn Val Pro Glu Ser Pro Asp Arg
            420                 425                 430

Lys Lys Arg Lys Arg Lys Ile Ser Val Gln Ala Gln Lys Gly Asp
        435                 440                 445

Phe Arg Lys Ile Phe Thr Glu Glu Asn Pro Lys Val Thr Leu Trp
    450                 455                 460

Ile Phe Thr Val Leu Ser Ser Pro Val Val Arg Arg Lys Gly Phe
465                 470                 475                 480

Tyr Ile Arg Arg Lys Asn Thr Asp Pro Gln Ser Ala Phe Gly Met Arg
                485                 490                 495

Met Glu Leu Gly His Gln Met Asn Leu Lys Ser Lys Glu Lys Glu Gly
            500                 505                 510

Thr Gln Arg Thr Gly Asn Gly Ile Tyr Val Val Lys Glu Arg Pro Glu
        515                 520                 525

Ser Cys Arg Val Asp Phe Ala Leu Ser Ser Lys Asn Lys Ser Gln Glu
    530                 535                 540

Arg Val Lys Gln Val Asn Phe Tyr Tyr Pro Leu Ser His His Val Ala
545                 550                 555                 560

Asp Phe Pro Cys Leu Glu Ala His Leu Arg Ala Ser Glu Phe Pro Ser
                565                 570                 575

Ser Glu Ser Pro Pro His Leu Gly Met Ala Ser Ser Lys Gln Leu Ile
            580                 585                 590

Cys Ile Val Asn Leu Gly Trp Gly Ser Lys Leu Asn Lys Asn Met Lys
        595                 600                 605

Lys Arg
    610

<210> SEQ ID NO 9
<211> LENGTH: 599
<212> TYPE: PRT
<213> ORGANISM: Homo sapiens

<400> SEQUENCE: 9

Val Thr Leu Pro Ile Leu Arg Ser Asp Pro Cys Pro Ser Pro Trp Lys
1               5                   10                  15

Ala Arg Asn Asp Lys Leu Lys Val Gln Asp Val His His Asp Lys Ser
            20                  25                  30

His Gly Arg Gly Ser Phe Ser Ala Leu His Ala Pro Glu Ala Gly Asp
        35                  40                  45

Arg Leu Cys His Thr Gln Ala Ile Ser Leu Leu Arg Pro Pro Arg Gln
    50                  55                  60

Leu His His His Glu Asn Val His Gly Ile Ser Gly Ser Leu Lys Phe
65                  70                  75                  80

Asp Pro Cys Ile Gln Ser Gly Ala Gln His Ser His Pro Thr Gly Glu
                85                  90                  95

Asp Phe Pro Val Ser Ser Gly Asp Ile Val Gln Ser Asn Pro Ala Ile
```

-continued

```
                    100                 105                 110
Ser Gln Ser Gly Asp Asp Leu Gln Lys Leu Gln Thr Cys Trp Cys Phe
            115                 120                 125
Leu Thr Ala Glu Gln Arg His Thr Asn Pro Thr Ser Pro Asn Trp Pro
        130                 135                 140
Ser Arg Arg Lys Leu Pro Pro Tyr Pro Thr Gly Ala Ala Pro Pro Gln
145                 150                 155                 160
Thr Pro Ser Thr Lys Leu Phe Thr Leu Cys Ala Lys Ser Gln Ala Trp
                165                 170                 175
Asn Ile Leu Pro Ala Lys His Asp Pro Glu Val Ala Gln Pro Ile Pro
            180                 185                 190
Cys Pro Ala Ser Pro Cys Thr His Pro Gly Arg Lys Lys His Phe Ser
        195                 200                 205
Asp Gln Gln Val Asn Ile Gln Asn Glu Cys Gly Arg Arg Leu Arg Arg
    210                 215                 220
Asp Ala Gln Pro Pro His His Cys Ala Ser Gly Gln Gln Pro Asp Pro
225                 230                 235                 240
Pro Asn Lys Arg Arg Arg Pro Ser Arg Asp Ala Pro Leu Ser Leu Gly
                245                 250                 255
Leu Tyr Ala Arg Asp Lys Arg Phe Ser Arg Thr Lys Pro Arg Arg Ala
            260                 265                 270
Pro Gly Gly Val Gln His Thr Phe Arg Gln Glu Arg Lys Glu Lys Lys
        275                 280                 285
Lys Met Tyr Leu Val Asn Ser Lys Lys Glu Thr Glu Lys Lys Pro Pro
    290                 295                 300
Lys Arg Asp Ser Leu Ile Thr Arg Asn Pro Lys Glu Ala Gln Lys Gly
305                 310                 315                 320
Gly Ser Gly Ser Ser Lys Glu Arg Leu Asn Leu Leu His Gly Arg Asp
                325                 330                 335
Lys Gly Pro Lys Gly Glu Asn Met Cys Pro Lys Val Glu Ile Arg Gly
            340                 345                 350
Asp His Trp His Phe Arg Asn Glu Arg Lys Glu Val Pro Glu Asp Ala
        355                 360                 365
Tyr Thr Thr Lys Gly His Thr Arg Gly Ser Leu Thr Trp Ala Trp His
    370                 375                 380
Pro Arg Glu Ala Pro Ser Gly Gly Asp Ser Lys Glu Arg Arg Leu
385                 390                 395                 400
Asn Leu Glu Leu Arg Gly His Asp Glu Gly Pro Lys Gly Lys Asn Met
                405                 410                 415
Cys Pro Lys Val Gln Ile Glu Arg Lys Glu Lys Gly Glu Arg Tyr Leu
            420                 425                 430
Phe Lys Leu Lys Lys Glu Ile Ser Glu Lys Tyr Ser Pro Lys Arg Lys
        435                 440                 445
Thr Gln Lys His Cys Gly Phe Ser Leu Phe Ala Pro Arg Asp Leu Trp
    450                 455                 460
Gly Glu Arg Asp Phe Ile Glu Glu Asn Glu Thr Arg Ile Leu Ser Glu
465                 470                 475                 480
Val His Ser Glu Gly Trp Asn Leu Val Asn Thr Lys Ile Ser Arg Arg
                485                 490                 495
Lys Arg Lys Glu Arg Lys Glu Leu Glu Thr Glu Tyr Thr Leu Arg Asn
            500                 505                 510
Asp Pro Arg Arg Ala Ala Glu Glu Trp Thr Leu Leu Cys Pro Pro Arg
        515                 520                 525
```

```
Ile Asn Leu Lys Arg Glu Leu Asn Ser Lys Ile Ser Thr Thr Leu Ser
    530                 535                 540

Val Thr Met Leu Gln Thr Phe Pro Val Trp Arg Leu Thr Leu Glu Leu
545                 550                 555                 560

Leu Ser Phe Gln Ala Leu Ser His Leu His Ile Trp Ala Trp His Leu
                565                 570                 575

Gln Asn Asn Phe Ala Leu Ile Trp Asp Gly Glu Ala Asn Asp Ser Lys
                580                 585                 590

Ile Lys Ile Lys Lys Ser Ala
        595
```

```
<210> SEQ ID NO 10
<211> LENGTH: 29
<212> TYPE: DNA
<213> ORGANISM: Artificial Sequence
<220> FEATURE:
<223> OTHER INFORMATION: Synthetically generated oligonucleotide

<400> SEQUENCE: 10
ttgaattcat ggaagaggct cttttttcag                                    29

<210> SEQ ID NO 11
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 11
ttgaattcct tctgctaggc cagttgg                                       27

<210> SEQ ID NO 12
<211> LENGTH: 13
<212> TYPE: DNA
<213> ORGANISM: Artificial Sequence
<220> FEATURE:
<223> OTHER INFORMATION: Synthetically generated oligonucleotide

<400> SEQUENCE: 12
agggaaaagg tca                                                      13

<210> SEQ ID NO 13
<211> LENGTH: 13
<212> TYPE: DNA
<213> ORGANISM: Artificial Sequence
<220> FEATURE:
<223> OTHER INFORMATION: Synthetically generated oligonucleotide

<400> SEQUENCE: 13
agggaaaacc tca                                                      13

<210> SEQ ID NO 14
<211> LENGTH: 2336
<212> TYPE: DNA
<213> ORGANISM: Homo sapiens

<400> SEQUENCE: 14
tagatataga cttttaaagg taaaagaaa gaataaagat ggagggtgtg ataatcctat    60
gaagtgtctg ggtttgggtc ctgagggcag ccaattacat cccagactca ctggcaatca   120
acagtccaag ccagggtccc atcagctgaa tcctgaggtc ggggatgctt cagtctttac   180
agaacagggt caaggaagag tccagaaacc gccgtcattg gcttcatgaa aaccgagcac   240
```

```
gtctttgaga tcttttttcaa attctgcctc taagtcaagt cctacctggc caaagtcaga    300
agccttgtaa aatgttttat ggttgcgaaa catcaggcgc atgtctcgca caaaccatgc    360
caccgtgtac atttccgtaa tcagccttc cttaaccagg tccaaccaca ttgcttcctg    420
aaagggctca ccgtaatctc gaatcagctg gtcctgaggc tgcatctgcc tctccagggt   480
cttagataca tgatggcact gttggcttcc tgaagacctc ttcatcctgc agaaggtgca   540
actccacagc atcctcttgg cttccacagg ggggatgtga cagtcctcat ggaagactcg   600
tggacaagta ccgcagcaga gaagttgtcc cccttgacag cacacctcgc attcatccga   660
gttttttccgc ttcagcagct ctcctagggt cgttccttca aacgtatat tccgtttcca    720
gttctttgcg ttccttcctt ttccttcgac ttcaaaattca tttggtgtta accaagttcc   780
atcctcattc cgaatgcact tcactgagga tccgtgtttc attttcttct tatataaaat   840
ccctttcgcc tcaccacagg tcacgggag cttagaacag tgaaaatcca cagtgtcact    900
tttgggtttt cctcttcggt gaatattttt ctgaaatctc cttttttgagc ttgaacagat    960
atctttctcc ttttttcttt tctttcgatct ggactttcgg gcacatttag ttcttgcctt   1020
ttggaccctc atcatgacct ctgagttcca ggttgagtcg tctttccttt gagtcacctt   1080
atccaccact tggagcttct cttggatgcc atgcccaggt gaggctgccc cttgtgtgac   1140
ccttcgtggt gtactaggcg tctctgggaa cctctttcct tcattcattt ctgaagtgcc   1200
atcaatgatc tcctctgatc tcgactttcg ggcacattca gttctcgcct tttgggccct   1260
tgtctctacc gtggagttac aagttgagtc atctttcttt tgaggaacct gatccaccct   1320
tttgagcttc ttttggattc cgtgtctaga tgaggctgtc cctcttggga ggcttttttt   1380
cttatgtctc ctttttggag ttgaccagat acatctttt cttttcttc ctttcttgtc    1440
tgaaggtgtg ctggacacct cctggggctc ttctgggtca tttggttctg agaattatc   1500
tcttatctct ggcatagagc ccaagggaga gtggggcatc tcttgagggt cttctttatc   1560
tcttatttgg gggatcaggt tgtcactggc cacttgcaca gtgctagtga ggaggctggg   1620
catctcttct gagtcttctt ccgcattcat tttggatgtt aacttgtcat ggtcactga    1680
agtgcttctt ccttcctgga tgagtgcagg gagaggcagg acagggtcag atgggctggg   1740
cgactcactc aggatctcag tgctttgctg ggaggatgtt ccaggctcac tgactcttgg   1800
cgcacagggt gaacagcttg gttgaggggg tttgtggtgg ggcagcgcca gtgggtatg   1860
gagggagctt ccttctgcta ggccagttgg ggcttcaagt aggattggtg tgtctctgct   1920
ctgccgttca taggaagcac caacacgttt gaagcttctg taaatcgtca ccagattggg   1980
atattcacgc aggttaattt gactgaacaa tgtcaccaga agagacaggt taaaagtcct   2040
ctccagttgg gtgagaatgt tgtgcaccac tctggataca gggatcaaat ttctacaggc   2100
ttccagagat tccatgtaca ttctcttagt gatgatggag ttgtctagga ggccttcaaa   2160
gaagggaaat ggcttgtgta tggcataggc gatccccagc ttctggtgca tgaagtgctg   2220
aaaaagagcc tcttccatgg ctcttgtcat ggtgaacatc ctggactttg agtttgtcgt   2280
tcctcgcttt ccaggggctg ggacagggat cactcctcaa gattgggaga gttaca       2336
```

<210> SEQ ID NO 15
<211> LENGTH: 1919
<212> TYPE: DNA
<213> ORGANISM: Homo sapiens

<400> SEQUENCE: 15

-continued

```
cggcgctttt tcatttaatt tttattttag agtcatttgc ttccccatcc caaattaact       60
atgcaaatta attgttttga agatgccatg cccaaatgtg gaggtgactc agagcttgga      120
aactcagaag ctctaaggtg agcctccaga cagggaaagt ctgcaacatg gtgactgaga      180
gggtagtaga aattcacttg ctatttaact ctctcttgag atttattctt ggaggacaga     240
gcaaagtcca ctcttcagca gctctcctag ggtcgttcct tcacaacgta tattccgttt     300
ccagttcttt gcgttccttc cttttccttc gacttcaaat tcatttggtg ttaaccaagt     360
tccatcctca ttccgaatgc acttcactga ggatccgtgt ttcattttct tcttatataa     420 aatcccttc gcctcaccac aggtcacggg gagcttagaa cagtgaaaat ccacagtgtc      480
acttttgggt tttcctcttc ggtgaatatt tttctgaaat ctccttttg agcttgaaca      540 gatatctttc tcctttttct tttctttcga tctggacttt cgggcacatt tagttcttgc    600
cttttggacc ctcatcatga cctctgagtt ccaggttgag tcgtctttcc tttgagtcac     660
cttatccacc acttggagct tctcttggat gccatgccca ggtgaggctg cccttgtgt      720 gaccttcgt ggtgtactag gcgtcttctg ggacctcttt ccttcattca tttctgaagt     780
gccatcaatg atctcctctg atctcgactt tcgggcacat tcagttctcg ccttttgggc    840
ccttgtctct accgtggagt tacaagttga gtcatctttc ttttgaggaa cctgatccac     900 cctttgagc ttcttttgga ttccgtgtct agatgaggct gtccctcttg ggaggcttt      960 tttcttatgt ctcctttttg gagttgacca gatacatctt tttcttttct ttcctttctt    1020
gtctgaaggt gtgctggaca cctcctgggg ctcttctggg tcatttggtt ctggagaatt    1080
atctcttatc tctggcatag agcccaaggg agagtggggc atctcttgag ggtcttcttt    1140
atctcttatt tggggatca ggttgtcact ggccacttgc acagtgctag tgaggaggct     1200
gggcatctct tctgagtctt cttccgcatt cattttggat gttaacttgt cattggtcac    1260
tgaagtgctt cttccttcct ggatgagtgc agggagaggc aggacagggt cagatgggct    1320
gggcgactca ctcaggatct cagtgctttg ctgggaggat gttccaggct cactgactct    1380
tggcgcacag ggtgaacagc ttggttgagg gggtttgtgg tggggcagcg ccagtggggt    1440
atggagggag cttccttctg ctaggccagt tggggcttca agtaggattg gtgtgtctct    1500
gctctgccgt tcataggaag caccaacacg tttgaagctt ctgtaaatcg tcaccagatt    1560
gggatattca cgcaggttaa tttgactgaa caatgtcacc agaagagaca ggttaaaagt    1620
cctctccagt tgggtgagaa tgttgtgcac cactctggat acaggatca aatttctaca    1680 ggcttccaga gattccatgt acattctctt agtgatgatg gagttgtcta ggaggccttc    1740
aaagaaggga aatggcttgt gtatggcata ggcgatcccc agcttctggt gcatgaagtg    1800
ctgaaaaaga gcctcttcca tggctcttgt catggtgaac atcctggact ttgagtttgt    1860
cgttcctcgc tttccagggg ctgggacagg gatcactcct caagattggg agagttaca    1919
```

SP110, A POLYPEPTIDE COMPONENT OF THE NUCLEAR BODY

CROSS REFERENCE TO RELATED APPLICATIONS

The present application is a national phase application under 35 U.S.C. Section 371 filed from International Patent Application PCT/US01/23248, filed 24 Jul. 2001, which claims priority to U.S. provisional patent application Ser. No. 60/220,305, filed 24 Jul. 2000. The contents of these applications are incorporated herein by reference in their entirety.

FEDERALLY SPONSORED RESEARCH

Work on the invention was supported in part by National Institutes of Health grants AR-01866 and DK-051179. Therefore, the government has certain rights in the invention.

TECHNICAL FIELD

This invention relates to molecular biology, biochemistry, cell biology, medicine and medical diagnostics.

BACKGROUND

The nuclear body is a multiprotein complex located within the nuclei of cells. The nuclear body is also known as nuclear domain 10, PML oncogenic domain, and the Kr body. Immunohistochemical staining typically indicates 5–30 nuclear bodies within a nucleus. The nuclear bodies appear as discrete, punctate regions. The number of nuclear bodies in the cell, and the intensity of antibody staining of these structures, increase in response to heat shock and viral infection, as well as following exposure to interferons and heavy metals (Ascoli et al., *J. Cell Biol.* 112:785–795, 1991). The nuclear body appears to be involved in the regulation of gene transcription. Nascent RNA polymerase II transcripts have been found within the nuclear body (LaMorte et al., *Proc. Natl. Acad. Sci. USA* 95:4991–4996, 1998), and the nuclear body is a preferred site for transcription of viral genes (Ishov et al., *J. Cell. Biol.* 138:5–16, 1997).

Promyelocytic leukemia (PML) protein is a component of the nuclear body. PML protein is involved in several cellular processes. For example, PML protein regulates cell growth (Wang, et al., *Science* 279:1547–1551, 1998) and may mediate apoptosis (Wang, et al., *Nature Genetics* 20:266–272, 1998; Quignon et al., *Nature Genetics* 10:259–265, 1998). PML protein also recruits cAMP response element-binding protein (the CREB-binding protein or CBP) to the nuclear body and functions as a potent nuclear hormone receptor co-activator (Doucas et al., *Proc. Natl. Acad. Sci. USA* 96:2627–2632, 1999).

In addition to its involvement in gene transcription, the nuclear body is a target of autoantibodies in the sera of patients who have primary biliary cirrhosis (P BC), an autoimmune disease (Hodges et al., *Am. J. Hum. Genet.* 63:297–304, 199&; Melnick et al., *Blood* 93: 3167–3215, 1999; Stemsdorf et al., *Immunobiology* 198:307–331, 1997). PBC patients carry autoantibodies directed against Sp100 (Speckled 100 kDa), a polypeptide component of the nuclear body (Szostecki et al., *J. Immunol.* 145:4338–4347, 1990). Two splice variants of Sp100, designated Sp100b and Sp100-HMG, have also been found (Dent et al., *Blood* 88:1423–1436, 1996; Seeler et al. *Proc. Natl. Acad. Sci. USA.* 95:7316–7321, 1998; Lehining et al., *Proc. Natl. Acad. Sci. USA* 95:7322–7326, 1998). These proteins interact with members of the heterochromatin protein 1 (HP1) family of non-histone chromosomal proteins. When bound to a promoter, the Sp100 proteins and HP1 behave as transcriptional repressors in transfected cells. These observations suggest that the nuclear body in general, and the Sp100 proteins in particular, may maintain chromatin architecture and regulate gene transcription (Seeler, et al. *Proc. Natl. Acad. Sci. USA* 95:7316–7321, 1998 and Lehming et al., *Proc. Natl. Acad. Sci. USA* 95:7322–7326).

Sera from PBC patients have also been used to identify a leukocyte-specific component of the nuclear body designated Sp140 (Bloch et al., *J. Biol. Chem.* 46:29198–29204, 1996). The N-terminal portion of Sp140 exhibits sequence homology with the N-terminal segments of the Sp100 proteins. The middle region of Sp140 contains a "SAND" domain (Gibson et al., *Trends Biochem. Sci.* 23:242–244, 1998), and the C-terminal portion of Sp140 contains a plant homeobox domain and a bromodomain.

SUMMARY

A full length cDNA encoding Sp110 Speckled 110), a novel 110 kDa polypeptide, has been discovered and characterized. It has been discovered that Sp110 is a component of the nuclear body, is expressed in leukocytes, and is also expressed in other types of cells, including endothelial cells, smooth muscle cells, liver cells and heart cells, after contact with, cytokines, including tumor necrosis factor, interleukin 1, and interferons. Other discoveries include the following: Sp140 recruits Sp110 to the nuclear body, Sp110 functions as an activator of gene transcription, and Sp110 serves as a nuclear hormone receptor co-activator.

Based on these and other discoveries, the invention features an isolated DNA containing a nucleotide sequence whose complement hybridizes under stringent hybridization conditions to a DNA molecule whose nucleotide sequence consists of nucleotides 405 to 797 of the Sp110 cDNA (SEQ ID NO:1). In some embodiments, the isolated DNA also includes at least one of the following: a nucleotide sequence encoding a domain having at least 80% sequence identity with amino acids 6–109 (Sp100-like domain) of the Sp110 polypeptide (SEQ ID NO:2); a domain having at least 80% sequence identity with amino acids 454–532 of SEQ ID NO:2 (SAND domain); a domain having at least 80% sequence identity with amino acids 537–577 of SEQ ID NO:2 (plant homeobox domain); and a domain having at least 80% sequence identity with amino acids 606–674 of SEQ ID NO:2 (bromodomain).

In some embodiments, the DNA hybridizes as described above and includes a nucleotide sequence encoding at least one of the following: amino acids 6–109 of SEQ ID NO:2 (Sp100-like domain) or amino acids 6–109 of SEQ ID NO:2 with one or more, e.g., 5, 10, 15 or 20 conservative amino acid substitutions therein; amino acids 454–532 of SEQ ID NO:2 (SAND domain) or amino acids 454–532 of SEQ ID NO:2 with one or more, e.g., 5, 10, 15 or 20, conservative amino acid substitutions therein; amino acids 537–577 of SEQ ID NO:2 (plant homeobox domain) or amino acids 537–577 of SEQ ID NO:2 with one or more, e.g., 5, 10, 15 or 20, conservative amino acid substitutions therein; and amino acids 606–674 of SEQ ID NO:2 (bromodomain) or amino acids 606–674 of SEQ ID NO:2 with one or more, 5, 10, 15 or 20, conservative amino acid substitutions therein.

In some embodiments, the isolated DNA hybridizes as described above, and also includes a nucleotide sequence encoding all of the following: amino acids 6–109 of SEQ ID NO:2 (Sp100-like domain) or amino acids 6–109 of SEQ ID NO:2 with one or more conservative amino acid substitutions therein; amino acids 454–532 of SEQ ID NO:2 (SAND domain) or amino acids 454–532 of SEQ ID NO:2 with one or more conservative amino acid substitutions therein; amino acids 537–577 of SEQ ID NO:2 (plant homeobox domain) or amino acids 537–577 of SEQ ID NO:2 with one or more conservative amino acid substitutions therein; and amino acids 606–674 of SEQ ID NO:2 (bromodomain) or amino acids 606–674 of SEQ ID NO:2 with one or more conservative amino acid substitutions therein.

In some embodiments, the isolated DNA contains a nucleotide sequence that encodes a polypeptide whose amino acid sequence is the sequence set forth as SEQ ID NO:2 or the sequence set forth as SEQ ID NO:2, with one or more, e.g., 5, 10, 15 or 20 conservative amino acid substitutions therein.

In some embodiments, the isolated DNA hybridizes as described above and also includes a nucleotide sequence encoding an Sp110 inhibitor polypeptide containing: amino acids 6–109 of SEQ ID NO:2 (Sp100-like domain) or amino acids 6–109 of SEQ ID NO:2 with one or more conservative amino acid substitutions therein; amino acids 537–577 of SEQ ID NO:2 (plant homeobox domain) or amino acids 537–577 of SEQ ID NO:2 with one or more conservative amino acid substitutions therein; and amino acids 606–674 of SEQ ID NO:2 (bromodomain) or amino acids 606–674 of SEQ ID NO:2 with one or more conservative amino acid substitutions therein; wherein the polypeptide does not contain a SAND domain.

In some embodiments, the isolated DNA contains a nucleotide sequence (Sp110 splice variant) that encodes the amino acid sequence set forth as SEQ ID NO:5, or the sequence set forth as SEQ ID NO:5 with one or more, e.g., 5, 10, 15 or 20, conservative amino acid substitutions therein.

The invention also features a vector containing any of the DNAs described above, and a host cell containing the vector. In the vector, the DNA can be operably linked to one or more expression control sequences.

The invention also features a substantially pure polypeptide encoded by any of the DNAs described above. In addition, the invention includes a substantially pure polypeptide (an inhibitor of Sp110 activity) containing an Sp110 Sp100-like domain, an Sp110 SAND domain, an Sp110 plant homeobox domain, and an Sp110 bromodomain, wherein the sequence of amino acids 110 to 453 of SEQ ID NO:2 is not present. In some embodiments, this polypeptide includes a membrane transport moiety, i.e., a moiety that allows the polypeptide to enter a cell. Exemplary membrane transport moieties are an internalization peptide sequence derived from Antennapedia and an HIV tat peptide.

The invention also features antibodies that bind specifically to the Sp110 polypeptide. The antibodies can be labeled.

The invention also features a screening method for identifying a compound that inhibits Sp110 dimerization. The method, which can be in vitro, includes: providing an Sp110 polypeptide sample solution; adding to the sample solution a candidate compound; and detecting a decrease in Sp110 dimerization in the presence of the candidate compound, as compared to Sp110 dimerization in the absence of the candidate compound.

The invention also features a screening method for identifying a compound that enhances or promotes Sp110 dimerization. The method, which can be in vitro, includes: providing an Sp110 polypeptide sample solution; adding to the sample solution a candidate compound; and detecting an increase in Sp110 dimerization in the presence of the candidate compound, as compared to Sp110 dimerization in the absence of the candidate compound.

The invention also features a screening method for identifying a polypeptide that dimerizes with Sp110 to form an inactive heterodimer. The method includes: providing an Sp110 polypeptide sample solution; adding to the sample solution a candidate polypeptide, thereby forming a test mixture; providing a gene expression system comprising a reporter gene operably linked to an Sp110-responsive expression control sequence; contacting the test mixture with the gene expression system; and detecting a decrease in reporter gene expression level in the presence of the test mixture, as compared to gene expression level in the presence of the Sp110 polypeptide sample solution. The gene expression system can be in a living cell, e.g., a transformed host cell. Alternatively, the gene expression system can be in vitro, i.e., acellular.

The invention also features a screening method for identifying a polypeptide that dimerizes with Sp110 to form a constitutively active or hyperactive heterodimer. The method includes: providing an Sp110 polypeptide sample solution; adding to the sample solution a candidate polypeptide, thereby forming a test mixture; providing a gene expression system comprising a reporter gene operably linked to an Sp110-responsive expression control sequence; contacting the test mixture with the gene expression system (which can be cellular or acellular); and detecting a constitutive activity or an increase in reporter gene expression level in the presence of the test mixture, as compared to gene expression level in the presence of the Sp110 polypeptide sample solution.

The invention also features a screening method for identifying a compound or polypeptide that inhibits Sp110 binding to a nuclear hormone receptor. The method, which can be in vitro, includes: providing an Sp110 polypeptide sample solution; adding to the sample solution a candidate compound; adding to the sample solution a nuclear hormone receptor; and detecting a decrease in Sp110 binding to the nuclear hormone receptor in the presence of the candidate compound, as compared to Sp110 binding to the nuclear hormone receptor in the absence of the candidate compound.

The invention also features a screening method for identifying a compound or polypeptide that enhances Sp110 binding to a nuclear hormone receptor. The method, which can be in vitro, includes: providing an Sp110 polypeptide sample solution; adding to the sample solution a candidate compound; adding to the sample solution a nuclear hormone receptor; and detecting an increase in Sp110 binding to the nuclear hormone receptor in the presence of the candidate compound, as compared to Sp110 binding to the nuclear hormone receptor in the absence of the candidate compound.

The invention also features a screening method for identifying a compound or polypeptide that inhibits the binding of an Sp110 dimer to an Sp110-binding nucleotide sequence. The method, which can be in vitro, includes: providing an Sp110 polypeptide sample solution; adding to the sample solution a candidate compound or polypeptide; adding to the sample solution an Sp110-binding nucleotide sequence; and detecting a decrease in Sp110 binding to the Sp110-binding nucleotide sequence in the presence of the candidate compound, as compared to Sp110 binding to the Sp110-binding nucleotide sequence in the absence of the candidate compound.

The invention also features a screening method for identifying a compound or polypeptide that enhances or promotes the binding of an Sp110 dimer to an Sp110-binding nucleotide sequence. The method, which can be in vitro, includes: providing an Sp110 polypeptide sample solution; adding to the sample solution a candidate compound or polypeptide; adding to the sample solution an Sp110-binding nucleotide sequence; and detecting an increase in Sp110 binding to the Sp110-binding nucleotide sequence in the presence of the candidate compound, as compared to Sp110 binding to the Sp110-binding nucleotide sequence in the absence of the candidate compound.

The invention also features a method for diagnosing primary biliary cirrhosis (PBC) in a human patient. The method includes: providing a substantially pure Sp110 polypeptide; providing a serum sample from the patient; contacting Sp110 polypeptide with the serum sample; and detecting specific binding of an antibody in the serum with the Sp110 polypeptide as an indication of PBC.

Unless otherwise defined, all technical and scientific terms used herein have the same meaning as commonly understood by one of ordinary skill in the art to which this invention belongs. In case of conflict, the present application, including definitions, will control. All publications, patents and other references mentioned herein are incorporated by reference.

Although methods and materials similar or equivalent to those described herein can be used in the practice or testing of the present invention, the preferred methods and materials are described below. The materials, methods and examples are illustrative only and not intended to be limiting. Other features and advantages of the invention will be apparent from the detailed description and from the claims.

DESCRIPTION OF DRAWINGS

FIG. 1 is the nucleotide sequence of a full-length, human Sp110 cDNA (SEQ ID NO:1)

FIG. 2 is a comparison of the deduced amino acid sequences of Sp110 (SEQ ID NO:2) and Sp140 (SEQ ID NO:3). Shaded portions of the sequences indicate the Sp100-like domain, the SAND domain, the plant homeobox domain (PHD), and the bromodomain. Conserved cysteine/histidine residues within the PHD are marked with asterisks. A dashed box encloses a predicted nuclear localization sequence, and a solid box encloses the LXXLL-type nuclear hormone receptor interaction domain. The sequence of the interferon-inducible protein nuclear phosphoprotein 72 begins at amino acid-241 (met) and ends at amino acid 605 (leu), which are indicated by arrows.

FIG. 3 is the nucleotide sequence of the full-length, human Sp110 cDNA (SEQ ID NO:1) and the deduced amino acid sequence (reading frame c) of the Sp110 polypeptide (SEQ ID NO:2).

FIG. 4 is the nucleotide sequence of a human Sp110 splice variant cDNA (Sp110b) (SEQ ID NO:4) and the deduced amino acid sequence (reading frame c) of the Sp110b polypeptide (SEQ ID NO:5).

DETAILED DESCRIPTION

Figure 5:
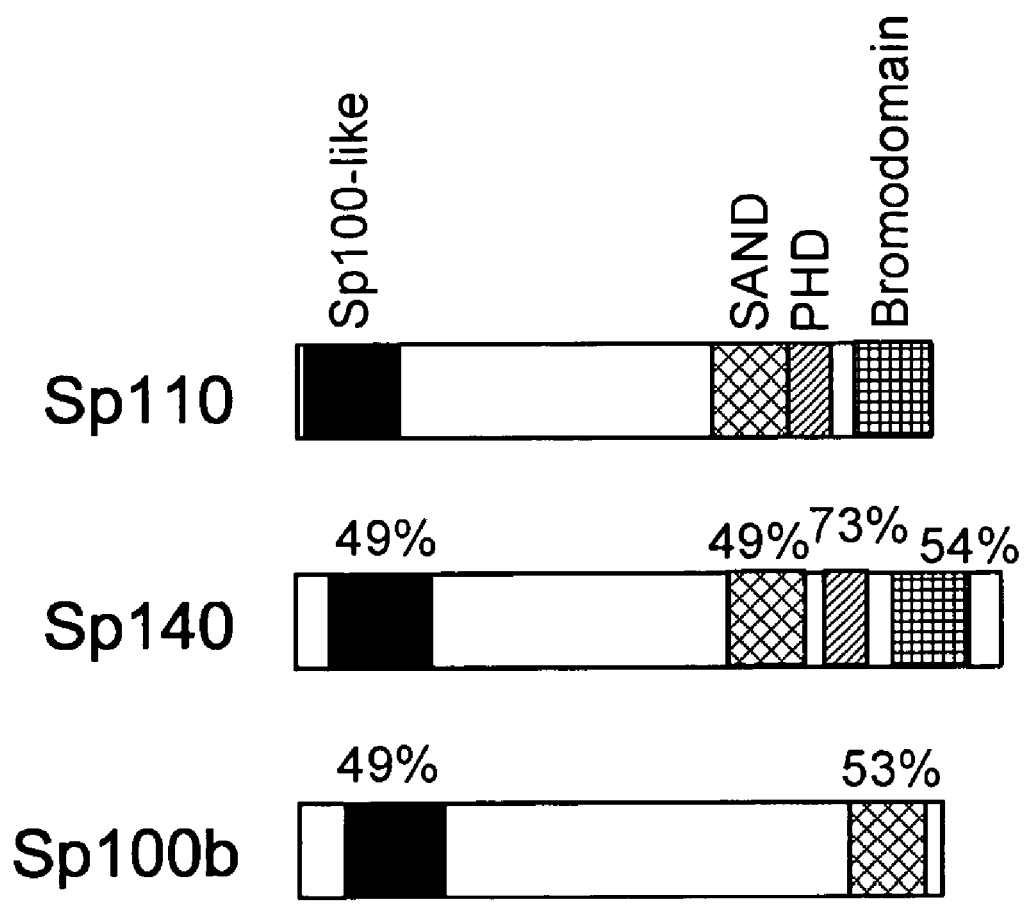
FIG. 5 is a schematic diagram comparing the domain structures of human Sp110, Sp140 and Sp100b. Also shown is the percent identity of the Sp110 domains, as compared to the corresponding domains in Sp140 and Sp100b.

The full-length, naturally-occurring, human Sp110 polypeptide includes an, Sp110-like domain (amino acids 6–109 of SEQ ID NO:2), a SAND domain (amino acids 454–532 of SEQ ID NO:2), a plant homeobox domain (PHD) (amino acids 537–577 of SEQ ID NO:2), and a bromodomain (amino acids 606–674 of SEQ ID NO:2). The full-length Sp110 functions as an activator of gene transcription. Sp110 also functions as a nuclear hormone receptor co-activator. Some embodiments of the invention include all of the domains in a single Sp110 polypeptide. In other embodiments, however, one or more of the domains is modified or absent.

The Sp100-like domain in the N-terminal portion of Sp110 has a potential helical motif, which can mediate homodimerization. (Seeler et al., *Proc. Natl. Acad. Sci. USA* 95:7316–7321, 1998). It is predicted that the Sp100-like domain in Sp110 functions in protein binding interactions, e.g., dimerization, with Sp140 or Sp100 to form a heterodimer, or dimerization with a second Sp110 polypeptide to form a homodimer. Therefore, a polypeptide that contains an Sp110 Sp100-like domain (or derivative thereof), but does not contain an activating domain, can be used in a cell to form inactive dimers comprising Sp140, Sp100 or Sp110. Such formation of inactive dimers reduces the availability of endogenous Sp140, Sp100 or Sp110 monomers for formation of active (transcription-activating or transcription-inhibiting) dimers, thereby reducing Sp140, Sp100, or Sp110 activity in the cell.

The Sp110 polypeptide is predicted to contain an activation domain located in the region between the Sp100-like domain and the SAND domain, i.e., in the region between amino acids 109 and 454 of SEQ ID NO:2. In some embodiments of the invention, a polypeptide containing this region or a derivative thereof is used to enhance or promote Sp110 activity.

Sp110 contains a SAND domain, variations of which are found in Sp100, Sp140, AIRE-1 (Nagamine et al., *Nature Genetics* 17:393–397, 1997), nuclear phosphoprotein 72, and DEAF-1 (Gross et al., *EMBO J.* 15:1961–1970, 1996). It is predicted that the Sp110 SAND domain is a DNA-binding domain (Gibson et al., *Trends Biochem. Sci.* 23:242–244, 1998). In some embodiments of the invention, a polypeptide that contains a SAND domain (or derivative thereof), but lacks an activating domain, is employed as an inhibitor of Sp110 activity in a cell, e.g., a cell cultured in vitro. An example is an Sp110 polypeptide lacking the region extending from approximately amino acid 110 to amino acid 453 in SEQ ID NO:2. Such a polypeptide inhibits Sp110 activity because the SAND domain occupies some or all of the Sp110 binding sites, thereby blocking access of active Sp110 molecules to the binding sites. In some embodiments, a membrane transport moiety, e.g., the internalization peptide sequence derived from Antennapedia (Bonfanti et al., *Cancer Res.* 57:1442–1446) or an HIV tat peptide (U.S. Pat. No. 5,652,122) is conjugated to the SAND domain to facilitate entry of the SAND domain into living cells. In other embodiments, the carrier moiety is a polypeptide fused to the SAND domain or polypeptide containing the SAND domain, e.g., at the amino terminus of the SAND domain-containing polypeptide.

The full-length Sp110 polypeptide contains a plant homeobox domain (PHD). This is a cysteine-rich region that spans 50–80 amino acid residues and contains the motif $Cys_4$-His-$Cys_3$ (Aasland et al., *Trends Biochem. Sci.* 20:56–59, 1995). This motif is found in many proteins that are involved in chromatin-mediated control of gene transcription. It is predicted that the Sp110 PHD functions in protein-protein or protein-DNA interactions.

The full-length Sp110 polypeptide contains a bromodomain. It is predicted that the Sp110 bromodomain functions catalytically in acetylation of histones. The bromodomain is an α helical motif found in many proteins involved in the regulation of gene transcription (Jeanmougin et al., *Trends Biochem. Sci.* 22:151–153, 1997). In general, the bromodomain is found in transcription factors that have catalytic domains. For example, SW12/SNF2 has a DNA-dependent ATPase domain (Laurent et al., *Genes Dev.* 7:583–591, 1993), $TAF_{II}250$ (Dickstein et al., *Cell* 84:781–790, 1996) and TIF1α (Fraser et al., *J. Biol. Chem.* 273:16199–16204, 1998) have kinase domains, and GCN5 has a histone acetyl-transferase (HAT) domain (Brownwell et al., Cell 84:843–851, 1996). The original description of the bromodomain reported a conserved motif spanning approximately 60 amino acid residues and containing two a helices (Haynes et al., *Nucl. Acids Res.* 20;2603, 1992). Subsequently it has been suggested that the bromodomain spans 110 amino acid residues and contains two additional a helices (Le Douarin et al., *EMBO J.* 15:6701–6715, 1996). The four predicted a helices were designated Z, A, B, and C. The Sp110 bromodomain of SEQ ID NO:2 includes the A, B, and C helices but lacks the Z helix. Some Sp110 splice variants may have a Z helix.

Sp110 polypeptides, and fragments and derivatives thereof, can be obtained by any suitable method. For example, Sp110 polypeptides can be produced using conventional recombinant DNA technology, as described in the Examples below. Guidance and information concerning methods and materials for production of polypeptides using recombinant DNA technology can be found in numerous treatises and reference manuals. See, e.g., Sambrook et al, 1989, *Molecular Cloning—A Laboratory Manual, $2^{nd}$ Ed.*, Cold Spring Harbor Press; Ausubel et al. (eds.), 1994, *Current Protocols in Molecular Biology*, John Wiley & Sons, Inc.; Innis et al. (eds.), 1990 *PCR Protocols*, Academic Press.

Alternatively, Sp110 polypeptides or fragments thereof can be obtained directly by chemical synthesis, e.g., using a commercial peptide synthesizer according to vendor's instructions. Methods and materials for chemical synthesis of polypeptides are well known in the art. See, e.g., Merrifield, 1963, "Solid Phase Synthesis," J. Am. Chem. Soc. 83:21492154.

Percent identity between amino acid sequences referred to herein is determined using the BLAST 2.0 program, which is available to the public through the website for the National Center for Biotechnology Information. Sequence comparison is performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., 1997, *Nucleic Acids Research* 25:3389–3402.

As used herein "isolated DNA" means DNA that has been separated from DNA that flanks the DNA in the genome of the organism in the which the DNA naturally occurs. The term therefore includes a recombinant DNA incorporated into a vector, e.g., a cloning vector or an expression vector. The term also includes a molecule such as a cDNA, a genomic fragment, a fragment produced by PCR, or a restriction fragment. The term also includes a recombinant nucleotide sequence that is part of a hybrid gene construct, i.e., a gene construct encoding a fusion protein.

As used herein, "high stringency" means the following: hybridization at 42° C. in the presence of 50% formamide; a first wash at 65° C. with 2×SSC containing 1% SDS; followed by a second wash at 65° C. with 0.1×SSC.

As used herein, "substantially pure polypeptide" means a polypeptide separated from components that naturally accompany it. For example, a polypeptide is substantially pure when it is at least 80%, by weight, free from the proteins and other organic molecules with which it is naturally associated. Purity can be measured by any suitable method, e.g., column chromatography, polyacrylamide gel electrophoresis, or HPLC analysis. A chemically synthesized polypeptide or a recombinant polypeptide produced in a cell type other than the cell type in which it naturally occurs is, by definition, substantially free from components that naturally accompany it.

As used herein, "conservative amino acid substitution" means a substitution within an amino acid family. Families of amino acid residues are recognized in the art and are based on physical and chemical properties of the amino acid side chains. Families include the following: amino acids with basic side chains (e.g. lysine, arginine, and histidine); amino acids with acidic side chains (e.g., aspartic acid and glutamic acid); amino acids with uncharged polar side chains (e.g. glycine, asparagine, glutamine, serine, threonine, tyrosine, and cysteine); amino acids with nonpolar side chains (e.g. alanine, valine, leucine, isoleucine, proline, phenylalanine, methionine, and tryptophan); amino acids with branched side chains (e.g., threonine, valine, and isoleucine); and amino acids with aromatic side chains (e.g., tyrosine, phenylalanine, tryptophan, and histidine). An amino acid can belong to more than one family.

A full-length Sp110 polypeptide, Sp110 polypeptide fragments containing individual Sp110 domains, or other antigenic Sp110 fragments, can be used to produce Sp110-specific antibodies. An example of an Sp110 fragment that can be used to elicit Sp110-specific antibodies is a polypeptide consisting of amino acids 219–235 of SEQ ID NO:2. The Sp110 specific antibodies can be readily obtained, without undue experimentation, through application of conventional techniques.

In view of its production by cells involved in host defense, i.e., leukocytes, and its induction by interferon (IFN) and cytokines, Sp110 appears to play a role in inhibiting viral replication and facilitating differentiation of cells, e.g., myeloid cells, and activation of cells involved in host defense. For example, an Sp110 polypeptide can be used therapeutically to treat myeloid malignancies by virtue of its ability to promote myeloid cell differentiation. In addition, the nuclear body, of which Sp110 is a structural component, is disrupted in various human disorders, including acute promyelocytic leukemia and viral infections. Therefore, in some embodiments of the invention, an Sp110 polypeptide (or derivative thereof) is introduced into a cell in vitro or in a mammal to enhance cellular defense mechanisms. In other embodiments, Sp110 is administered therapeutically to treat inflammation or to achieve alteration in lipid profiles.

A preformed Sp110 polypeptide can be introduced into a cell using conventional techniques for transporting proteins into intact cells, e.g., by fusing the polypeptide to the internalization peptide sequence derived from Antenntapedia (Bonfanti et al., *Cancer Res.* 57:1442–1446) or to an HIV tat peptide (U.S. Pat. No. 5,652,122). Alternatively, the Sp110 polypeptide can be expressed in the cell following introduction of an Sp110-encoding DNA, e.g., in a conventional expression vector, according to the invention. In some embodiments, Sp140 is concurrently introduced into the cell, or co-expressed in the cell, so that the Sp140 can recruit the Sp110 into nuclear bodies.

The biological activities of Sp110 include co-activation of nuclear hormone receptors, e.g., retinoic acid receptors (RARs), RXRs, LXR, FXR, peroxisome proliferator-activated receptors (PPARs), including PPARα and PPARγ, glucocorticoid receptors, estrogen receptors, progesterone receptors, androgen receptors, and orphan nuclear hormone receptors. Nuclear hormone receptors mediate signal transduction in various cellular responses. Sp110 appears to enhance expression of nuclear hormone-responsive genes by binding to a nucleotide sequence adjacent to the nuclear hormone response element and directly or indirectly enhancing gene expression. Activities of RARs and RXRs are important in cellular differentiation. Activities of PPARα and PPARγ are important in fatty acid metabolism and inflammation. Activities of FXR and LXR are important for cholesterol metabolism.

Where increased co-activation of an Sp110-responsive nuclear hormone receptor is needed, e.g., to enhance PPARα-mediated inhibition of the inflammatory response in smooth muscle cells or endothelial cells, an Sp110 polypeptide can be supplied in a therapeutic method. Similarly, in cardiac myocytes, Sp110 may augment PPARα's effect on lipid metabolism, potentially attenuating cardiac hypertrophy. Moreover, in adipocytes Sp110 may alter PPARγ regulation of lipid storage, potentially treating obesity.

Sometimes a nuclear hormone receptor-mediated response needs to be limited or reduced therapeutically. For example, an Sp110 derivative can be used to inhibit FXR receptors, thereby enhancing conversion of cholesterol to bile acids. In another example, Sp110 is used to block estrogen receptors in treatment of estrogen responsive tumors. The invention includes inhibitors of Sp110 activity, screening methods for identifying inhibitors of Sp110 activity, and methods of inhibiting Sp110 activity in, cells in vitro or in a mammal Inhibition of Sp110 activity can be accomplished through approaches including the following: a polypeptide that dimerizes with endogenous Sp110 polypeptides to form an inactive dimer; a small molecule (MW=1000 Da or less) that interferes with Sp110 dimerization; a polypeptide that occupies Sp110 binding sites (nucleotide sequences) in DNA without causing transcriptional activation; and a small molecule that interferes with Sp110-nuclear hormone receptor interactions.

An example of a polypeptide predicted to dimerize with endogenous Sp110 polypeptides to form an inactive dimer is a polypeptide that includes amino acids 1–453 of the Sp110 sequence fused to amino acids 533–689 of the Sp110 sequence (amino acids 1–453 of SEQ ID NO:2 fused to amino acids 533–689 of SEQ ID NO:2). Such a polypeptide includes the entire Sp110 amino acid sequence except the Sp110 SAND domain, which is predicted to be required for recognizing and binding to Sp110 binding sites in DNA, but not required for Sp110 dimerization.

An example of a polypeptide predicted to recognize and occupy Sp110 binding sites (nucleotide sequences) in DNA without causing transcriptional activation is an Sp110 SAND domain or fragment thereof.

Polypeptides and other molecules, e.g., small molecules, that inhibit or promote Sp110 activity can be identified by screening methods provided by the invention. The type of screening method employed will depend on the type of inhibition mechanism chosen. One general approach is based on Sp110 dimerization, which is predicted to be necessary for Sp110 biological activity. One variation on this approach is to provide a molecule that interferes with Sp110 dimerization. Another variation on this approach is to provide a polypeptide that dimerizes with endogenous Sp110 polypeptides to form an inactive dimer. A second general approach is to provide a molecule that binds to (blocks) a site on the Sp110 polypeptide that interacts with nuclear hormone receptors. A third general approach is to interfere with binding of active Sp110 dimers to Sp110-binding DNA sequences in the genome. One variation on this approach is to provide a molecule, e.g., a polypeptide, that binds to (blocks) Sp110-binding DNA sequences. Another variation on this approach is to provide an oigonucleotide based on an Sp110-binding DNA sequence in the genome. The oligonucleotide binds to (blocks) the DNA-binding site(s) on the Sp110 dimer.

Primary biliary cirrhosis (PBC) is an autoimmune disease that predominantly affects intrahepatic bile ducts. As with many other autoimmune diseases, the vast majority of patients with PBC are women and the etiology of this disorder is unknown. The natural history of PBC is one of slowly progressive cholestasis with the development of cirrhosis and death unless the patient undergoes liver transplantation. Disease progression in an individual patient, however, is highly variable and a pre-symptomatic phase may last longer than 20 years (Springer et al., *Am. J. Gastroenterol.* 94:47–53,1999 and Mahl et al., *J. Hepatol.* 20:707–713, 1994). Because of the variable course of patients with PBC and the availability of novel treatments for this disease, it is important to identify prognostic factors that may distinguish those patients with mild disease (who may not require treatment) from those with a more aggressive, rapidly progressive, illness.

The invention provides methods for identifying and characterizing novel autoantibody markers of disease state and prognosis in PBC patients. Serum samples from PBC patients are tested for the presence of antibodies that react with Sp110. Various types of methods for detecting and quantifying such antibody-antigen reactions are known and can be employed.

In some embodiments of the invention, PBC-related autoantibodies are detected and characterized in methods such as conventional immunoblotting (Western) techniques, wherein an Sp110 polypeptide (or Sp110 polypeptide fragment) is employed as an antigen. Typically, the Sp110 polypeptide is subjected to SDS-polyacrylamide gel electrophoresis (SDS-PAGE) and blotted (transferred) onto a suitable membrane, e.g., nitrocellulose, where the Sp110 antigen is immobilized. Sera from PBC patients are diluted as necessary and contacted with the Sp110 antigen-bearing membrane under suitable conditions for specific binding of the immobilized antigen to an anti-Sp110 antigen, if one is present. After suitable washing steps, bound antibody is detected.

Detection of bound antibody can be accomplished by any suitable method. For example, labeled protein A, which binds to IgG with high specificity and high affinity, can be used. The protein A can be labeled in any of various ways. Useful types of label include a conjugated calorimetric enzyme, e.g., horseradish peroxidase, a conjugated fluorochrome, e.g., FITC, or a radioactive atom, e.g., $^{125}$I. Immunoblot assay results can be quantitated, for example, by incorporating internal standards and a suitable optical scanning device. Preferably, suitable positive and negative controls are employed in testing patient sera. In addition to Sp110, other nuclear body components such as Sp100, Sp140 polypeptides can be tested simultaneously, e.g., on the same immunoblot membrane.

In some embodiments of the invention, PBC-related autoantibodies are detected and quantitated using techniques designed for rapid, high-volume screening, e.g., microtiter plate ELISA techniques. Such techniques are known in the art and can be employed in practicing the present invention without undue experimentation.

EXAMPLES

The invention is further illustrated by the following experimental examples. The examples are provided for illustrative purposes only, and are not to be construed as limiting the scope or content of the invention in any way.

Example 1

Isolation and Characterization of cDNA Clones Encoding Sp110

A nucleotide sequence in the EST database that encodes a polypeptide homologous to the N-terminal portions of Sp100 and Sp140 was obtained from the IMAGE consortium (accession number AA431918). This material proved unsuitable to prepare probes for screening a cDNA library because it was highly contaminated with unrelated cDNAs. Accordingly, two oligonucleotides were synthesized based upon the sequence of the EST clone (5'-TTGAATTCATG-GAAGAGGCTCTTTTTCAG-3' (SEQ ID NO:10) and 5'-TTGAATTCCTTCTGCTAGGCCAGTTGG-3' (SEQ ID NO:11)) and the polymerase chain reaction (PCR) was used to synthesize a fragment of the cDNA. The PCR product was radiolabeled and used to screen a λGT10 cDNA library prepared from human spleen (Clontech, Palo Alto, Calif.). Six cDNA clones from among approximately one million bacteriophages hybridized with the radiolabeled probe and were isolated by plaque purification. Bacteriophage growth, DNA isolation, and subcloning into pUC19 were performed using standard procedures (Sambrook et al, 1989, *Molecular Cloning—A Laboratory Manual*, $2^{nd}$ Ed., Cold Spring Harbor Press, 1989). The nucleotide sequence of the full-length cDNA was determined by the dideoxy chain termination method (Sanger et al., *Science* 214:1205–1210, 1981). The sequences of the six clones, when assembled, revealed the sequence of the fall length Sp110 cDNA (FIG. 1).

The cDNA encoding Sp110 was 2,337 base pairs long, with an open reading frame from nucleotides 78 to 2144 encoding a protein containing 689 amino acids (FIGS. 1 and 3). The start codon was preceded by an in-frame stop codon, indicating that this is a full-length cDNA. The amino acid residues at 241 to 605 of Sp110 were essentially identical to residues 1 to 365 of a previously reported polypeptide designated nuclear phosphoprotein 72 (Kadereit et al., *J. Biol. Chem.* 268: 24432–24441, 1993). In this region, the amino acid sequence of Sp110 differed from that of nuclear phosphoprotein 72 at amino acid 580 (I-M).

The N-terminal portion of Sp110, between amino acid residues 6 and 159 was 49% identical to the N-terminal portions of both Sp100 (Szostecki et al., *J. Immunol.* 145: 4338-4347, 1990) and Sp140 (Bloch et al., *J. Biol. Chem.* 46:29198–29204, 1996). A second region of homology between Sp110 and both Sp100b and Sp140 was present between amino acid residues 452 and 532. In this region, Sp110 was 53% identical to Sp100b (Dent et al., *Blood* 88:1423–1436, 1996) and 49% identical to Sp140. This portion of Sp100b and Sp140 was previously designated a SAND domain (Gibson et al., *Trends Biochem Sci.* 23:242–244, 1998). Sp110 amino acid residues 537 to 577 spanned a plant homeobox domain (Aasland et al., *Trends Biochem. Sci.* 20:56–59, 1995), and amino acid residues 606 to 674 contained the A, B, and C helices of a bromodomain (Jeanmougin et al., *Trends Biochem Sci.* 22:151–153, 1997). The plant homeobox domain and bromodomain of Sp110 were 71% and 54% identical to the corresponding regions in Sp140. In addition, these portions of Sp110 were 56% and 46% identical to the corresponding regions in murine TIF1α.

Example 2

Expression of Sp110 in Human Tissues and Cell Lines

The level of Sp110 mRNA in human tissues was determined by hybridizing membranes containing 2.5 µg of poly(A)$^+$-selected RNA from human tissues (multiple tissue Northern blots, Clontech Laboratories, Palo Alto, Calif.) with a $^{32}$P-radiolabeled 1.4 kb XbaI restriction fragment of the Sp110 cDNA. The human tissues represented on the membranes were spleen, thymus, prostate, testis, ovary, small intestine, colon, and peripheral blood leukocytes. The membranes were washed under stringent conditions and exposed to autoradiographic film for one hour. To confirm the presence of poly(A)$^+$-selected RNA in each lane, the membranes were hybridized with a $^{32}$P-radiolabeled β-actin cDNA probe. The membranes were washed under stringent conditions and exposed to autoradiography film for 30 minutes.

High levels of Sp110 mRNA were detected in human peripheral blood leukocytes and spleen. In contrast, lower levels of Sp110 mRNA were observed in thymus, prostate, testis, ovary, small intestine, and colon. In addition, low levels of Sp110 mRNA were observed in human heart, brain, placenta, lung, liver, skeletal muscle, kidney, and pancreas.

To investigate the expression of Sp110 in cells of the monocyte/granulocyte lineage, RNA was prepared from the myeloid precursor cell lines HL60 and NB4 (HL60 cells are available from the American Type Culture Collection, Manassas, Va.). RNA was extracted from these cell lines using the guanidinium isothiocyanate-cesium chloride method (Sambrook et al., Cold Spring Harbor Laboratory, Cold Spring Harbor, N.Y., 1989). The HL60 cells were maintained in RPMI supplemented with 10% fetal calf serum, L-glutamine (2 mM), penicillin (200 units/ml), and streptomycin (200 mg/ml). RNA was fractionated in formaldehyde-agarose gels (5 µg/lane) and equal loading of RNA was confirmed by staining 28S and 18S ribosomal RNA with ethidium bromide. RNA was transferred to nylon membranes and the membranes were hybridized with the radiolabeled XbaI restriction fragment of the Sp110 cDNA or the EcoRI/BamHI restriction fragment of the cDNA encoding human Sp100 (Bloch et al., *J. Biol. Chem.* 46:29198–29204, 1996). Membranes were washed and analyzed by autoradiography. Low levels of Sp110 mRNA were detected in both NB4 cells and HL60 cells.

To examine the effect of cellular differentiation on Sp110 mRNA, NB4 cells were treated for 48 hours with all trans retinoic acid (ATRA) (1 µM). Following this treatment, the level of Sp110 mRNA was increased in NB4 cells, which indicates that differentiation of NB4 cells is associated with increased expression of Sp110. To examine the effect of IFN-γ treatment on Sp110 mRNA levels, HL60 cells were treated with IFN-γ (200 units/ml) for 48 hours. A marked increase in Sp110 mRNA was observed. These results demonstrated that, as with Sp100, PML, and Sp140, IFN-γ-treatment enhances expression of Sp110.

Sp110 expression was also examined in human coronary artery smooth muscle cells (hCASMCs) and human umbilical vein endothelial, cells (HUVECs) following exposure to IFNα (200 u/ml). Expression of Sp110 mRNA was induced within 4 hours and reached a maximum level between 8 and 24 hours. Similar results were obtained after treating hCASMCs or HUVECs with IFNγ or IL-1β and TNFα. Sp110 gene expression was also markedly induced in hearts of mice treated with endotoxin, suggesting that inflammatory mediators increase Sp110 mRNA levels in cardiac myocytes.

The observation that Sp110 was expressed in human leukocytes and cytokine-treated human vascular cells suggested that Sp110 is present in cells that have important roles in the pathogenesis of atherosclerosis.

Example 3

Cellular Localization of Sp110

To study the cellular location of Sp110, antiserum directed against a recombinant fragment of Sp110 (amino acid residues 219 to 324) was generated in rats, and an adenovirus vector encoding Sp110 (Ad.Sp110) was prepared.

To construct an E1-deleted, recombinant adenovirus vector containing Sp110, the cDNA encoding Sp110 was cloned into the NotI and BamHI sites of pAd.RSV$_4$, which contained the Rous sarcoma virus long-terminal repeat promoter and the SV40 polyadenylation signal. The plasmid containing Sp110 was co-transfected into 2093 cells with pSM17. Homologous recombination between the two plasmids resulted in an adenovirus (Ad.Sp110) that contained Sp110 sequences in place of E1 sequences. Recombinant viruses in a plaque were amplified in 293 cells, and a high-titer stock was prepared. The 293 cells were grown in low glucose (1 g/L)-DMEM supplemented with 10% horse serum. The absence of replication-competent adenovirus in the viral stock was confirmed by the failure of Ad.Sp110 to produce cytopathic changes in A549 lung carcinoma cells. In addition, PCR failed to amplify a DNA fragment corresponding to the E1 region of adenovirus using oligonucleotides and the Ad.Sp110 stock. An adenovirus vector containing the cDNA encoding Sp140 was described previously in (Bloch, et al., *Mol. Cell. Biol.* 19:4423–4430,1999).

To produce antibodies directed against Sp110, three male Sprague-Dawley rats were immunized with recombinant protein containing amino acid residues 219–435 of Sp110 fused to glutathione-S-transferase (GST). The plasmid encoding this portion of Sp110 was prepared by ligating a BstYI/EcoRV restriction fragment of the cDNA encoding Sp110 into the BamHI/SmaI sites of pGEX (Pharmacia Biotech, Inc., Piscataway, N.J.). The plasmid was used to transform *E. coli*, and expression of the fusion protein was induced by treatment with isopropyl-1-thio-β-D-galactopyranoside. The fusion protein was purified from *E. coli* proteins as described in (Smith et al., *Gene* 67:31–40, 1988). Primary immunizations of three rats was performed using 50 μg of purified protein emulsified in complete Freund's adjuvant for each animal. Two subsequent booster injections consisting of 50 μg of protein were given at two-week intervals.

The rat anti-Sp110 antiserum reacted with Sp110 in extracts prepared from Ad.Sp110-infected HEp-2 cells, but not with Sp140 in extracts prepared from Ad.Sp140-infected HEp-2 cells or with Sp100, which is normally expressed in HEp-2 cells. In contrast, rat anti-Sp140 antiserum, previously prepared against amino acid residues 131–391 of Sp140 (Bloch et al., *J. Biol. Chem.* 46:29198–29204, 1996), reacted with Sp140, but not with Sp110 or Sp100. These results demonstrated that the rat anti-Sp110 antiserum was specific for Sp110.

To investigate the cellular location of Sp110, rat anti-Sp110 antibodies were used to stain NB4 cells before and after treatment with RA. Anti-Sp110 antiserum stained nuclear bodies in NB4 cells that were treated for 48 hours with ATRA (1 μM), but did not react with untreated NB4 cells.

To determine the location of Sp110 with respect to the PML/Sp100 nuclear body, NB4 cells were treated with ATRA and stained with rat anti-Sp110 antiserum and human serum containing antibodies directed against Sp100. Sp110 co-localized with Sp100 in nuclear bodies.

To further investigate the cellular location of Sp110, adenovirus-mediated gene transfer was used to express Sp1110 in human cell lines in which it is not normally expressed. At a multiplicity of infection (MOI) of 25 viruses per cell, approximately 25% of HEp-2 cells expressed levels of Sp110 that were detectable by indirect immunofluorescence. Surprisingly, Sp110 did not localize to nuclear bodies in these cells, but instead appeared to produce a granular nuclear staining pattern with prominent staining near the nuclear membrane. Cytoplasmic staining was also observed in a few cells. The contrasting results obtained using the leukocyte cell line NB4 and Ad.Sp110-infected HEp-2 cells can be reconciled with the present result if Sp140, another leukocyte-specific nuclear body component, recruits Sp110 to the nuclear body. HEp-2 cells were infected with both Ad.Sp140, at an MOI of 50, and Ad.Sp110, at an MOI of 25. At an MOI of 50, essentially all of the HEp-2 cells expressed detectable Sp140 within nuclear bodies. In cells infected with Ad.Sp140 alone, anti-Sp110 antiserum did not stain nuclear bodies, confirming that anti-Sp110 antiserum did not cross-react with Sp140. In cells infected with both Sp110 and Sp140, Sp110 localized to nuclear bodies and co-localized with Sp100-containing nuclear bodies. These results demonstrated that Sp140 enhances localization of Sp110 to the nuclear body.

Example 4

Transcriptional Activation by Sp110

The amino acid sequence motifs in Sp110, including the SAND domain, the PHD, and the bromodomain, suggested that Sp110 has a role in the regulation of gene transcription. To examine the potential effect of Sp110 on gene transcription, a eukaryotic expression plasmid encoding Sp110 fused to the DNA-binding domain of GAL4 (pBXG-Sp1110) was co-transfected with a CAT reporter plasmid containing five GAL4 binding sites and an SV40 enhancer region (pG5SV-BCAT) into COS cells. There was a dose-dependent increase in CAT activity in cells transfected with increasing amounts of pBXG-Sp110. These results are similar to those observed using pBXG-Sp140 and different from those obtained with pBXG-Sp100. The GAL4-Sp100 fusion protein was previously shown to inhibit CAT activity when co-transfected with the reporter plasmid (Seeler et al. *Proc. Natl. Acad. Sci. USA* 95:73167321, 1998; Lehming et al., *Proc. Nat. Acad. Sci. USA* 95:7322–7326, 1998; and Bloch, et al., *Mol. Cell. Biol.* 19:4423–4430, 1999). These results demonstrated that Sp110 is capable of modulating gene transcription and acts in these cells as a transcriptional activator.

Experiments were also performed to determine whether Sp110 could function as a retinoic acid receptor (RAR) transcriptional co-activator. When co-transfected into COS cells with a reporter gene containing three copies of the RARα response element, Sp110 significantly enhanced ATRA-induced expression of the reporter gene. Similar results were observed in studies using HeLa cells instead of COS cells. The extent of reporter gene activation by Sp110 was similar to that induced by the nuclear body component PML. These results demonstrated that Sp110 can function as a co-activator of the nuclear hormone receptor RAR.

Sp110 also acted as a co-activator of PPARα. When COS cells were co-transfected with PPARα and a reporter gene containing three copies of the PPAR response element (PPRE), Sp110 markedly enhanced agonist-induced expression of the reporter gene compared with the effect of PPARα expressed alone. Sp110 may interact with nuclear hormone receptors via an LXXLL domain. To determine whether Sp110 interacts with PPARα via the LULL domain, oligonucleotides and PCR were used to prepare a mutant Sp110 protein (Sp110m) in which two of the three leucine residues were changed, one to valine and one to alanine (LXXVA).

Although immunoblot studies demonstrated that Sp110 and Sp110m were expressed at similar levels in transfected COS cells the Sp110 mutant activated the PPARα receptor less than wild-type Sp110. These results demonstrated that Sp110 functions as a PPARα transcriptional co-activator and indicated that the interaction between Sp110 and PPARα may involve the LXXLL nuclear hormone receptor interaction domain.

Sp110 enhanced signal transduction through the retinoic acid receptor α (RARα) (LaMorte et al., *Proc Natl Acad Sci USA* 95:4991–4996, 1998) and, in contrast to the results obtained with PPARα, expression of Sp110m with RARα also enhanced expression of the reporter gene. Similarly, both Sp110 and the Sp110 mutant enhanced signal transduction through the PPARγ receptor. These results suggested that Sp110 had an effect on RARα signaling and PPARγ signaling, perhaps through interaction with nucleotide motifs adjacent to nuclear hormone receptor response element(s). Although the examples below involved the PPARα receptor, it is predicted that similar results will be achieved with other nuclear hormone receptors.

Example 5

PPARα Interaction with CBP/p300

PPARα interacted with the N-terminal portion of CBP/p300 between amino acid residues 39 and 221. To determine whether Sp110 also interacts with CBP, the mammalian two-hybrid system was used as an assay. In this assay, the GAL4 DNA-binding domain (GAL4) fused to CBP (GAL4-CBP) and a luciferase reporter gene containing GAL4 response elements were expressed in COS cells with either Sp110 fused to the herpes simplex virus VP16 activation domain (VP16-Sp110) or VP16 alone. Expression of VP16-Sp110 significantly enhanced Gal4-CBP-induced luciferase gene activity compared with VP16 alone. Thus, Sp110 interacts, either directly or indirectly, with CBP. The site of functional interaction between Sp110 and CBP was mapped more specifically to amino acid residues 271–720 of CBP. The Sp110-CBP functional interaction domain is therefore distinct from the PPARα-CBP interaction domain.

To identify the portion of Sp110 that functionally interacts with CBP, the N-terminal or C-terminal portions of Sp110 were fused to VP16 and expressed in COS cells together with GAL4CBP and a reporter gene. The C-terminal portion, which contained the PHD and the bromodomain, enhanced GAL4-CBP-induced expression of the reporter gene, but the N-terminal portion, which contained the Sp100-like region, did not. As described below, studies can be carried out to further delineate the domains that mediate functional interaction between Sp110 and CBP and to test whether Sp110 interacts with CBP directly.

Sp110 does not contain motifs, such as acetyltransferase (as in CBP/p300) or kinase domains (as in TIF1α), that are known to activate gene transcription. To identify the portion of Sp110 that enhances reporter gene expression, DNA segments encoding fragments of Sp110 fused to GAL4 were expressed with a reporter gene in COS cells. Neither the N-terminal (Sp100-like domain), nor the C-terminal (PHD/bromodomain) portions of Sp110 increased expression of the reporter gene. In contrast, fusion proteins containing the middle portion of the protein (putative activation domain and SAND domain) increased reporter gene expression. The mechanism by which Sp110 enhances PPARα-mediated gene transcription can be investigated, as described below, by identifying proteins that interact with the activation domain and SAND domain.

Example 6

Sp110 and Expression of Genes Regulated by PPARα

This experiment tests the possibility that Sp110 enhances expression of a reporter gene under the control of the native promoter region of CPTI, a gene that is regulated by PPARα, Co-transfection studies are performed in COS cells using a luciferase reporter construct that contains a CPTI gene promoter having the PPRE (AGGGAAaAGGTCA; SEQ ID NO:12). The effect of co-expression of Sp110 and PPARα on luciferase activity is compared to that of Sp110, PPARα or control vectors alone. An expected result is that Spl 10 enhances PPARα mediated expression of the reporter gene under the control of the CPTI promoter region.

Sp110 may enhance luciferase expression by interacting with other regulatory elements within the CPTI promoter region. To demonstrate that the effect of Sp110 on luciferase activity requires PPARα, the effect of Sp110 on a luciferase reporter plasmid that has a mutated PPRE (AGGGAAaAc-cTCA; SEQ ID NO:13), is determined. If Sp110 enhances CPTI promoter-driven luciferase activity by interacting with PPARα, then an expected result is that Sp110 has no effect on expression of the reporter plasmid with the mutated PPRE.

Example 7

Sp110 and PPARα Cooperation in Mitochondrial Fatty Acid Oxidation Gene Expression The fibroblast cell line 3T3-L1 can be induced to differentiate into cells that resemble white adipocytes. These cells normally express low levels of enzymes involved in mitochondrial fatty acid oxidation. To test the possibility that Sp110 enhances PPARα-mediated upregulation of mitochondrial fatty acid oxidation gene expression, Sp110 is overexptessed in 3T3-L1 cells using an adenovirus vector (Ad.Sp110). An unrelated protein, green fluorescent protein (GFP), is expressed as a control using a second adenovirus vector (Ad.GFP). 3T3-L1 cells will be infected with Ad.Sp110 or Ad.GFP at a virus MOI sufficient to produce infection of more than 90% of the cells. The cells are then incubated in medium containing insulin, 3-isobutyl-1-methylxanthine (IBMX), and dexamethasone to induce differentiation (Cao et al., *Genes Dev.*, 5:1538–1552, 1991). Immunobloting is performed to confirm successful transgene expression. RNA blot hybridization will be performed to measure the effect of Sp110 (compared with GFP) on expression of three fatty acid oxidation genes (MCAD, LCAD, and CPT-I) in the presence or absence of the PPAR(X agonist WY 14,643.

To examine the effect of Sp110 on the rate of fatty acid oxidation, 3T3 L1 cells are infected with either Ad.Sp110 or Ad.GFP, and the rate of palmitate oxidation is determined (Gulick et al., *Proc. Natl. Acad. Sci., USA*, 91:11012–11016, 1994). Seventy-two hours after infection, the cells are incubated with [$^{14}$C] palmitate. The tissue culture plates contain a central well with, a piece of filter paper. After 6 hours, the $^{14}CO_2$ is released from tissue culture medium by addition of 6 N HCl and $^{14}CO_2$ is collected overnight by alkalinization of the filter paper with 2 N NaOH. $^{14}CO_2$ is measured by scintillation counting of the filters.

Mutations in the LXXLL domain of Sp110 impair its ability to enhance PPARα-mediated expression of a reporter gene, most probably by blocking the direct interaction between PPARα and Sp110. To investigate the importance of the LXXLL domain in enhancing PPARα mediated gene expression, an adenovirus vector encoding Sp110m (Ad.Sp110m) is tested for its ability to induce expression of MCAD, LCAD, and CPT-I and to increase fatty acid oxidation in 3T3-L1 cells. The results of these tests with Ad.Sp110m are directly compared with those obtained using Ad.Sp110.

An expected result is that Sp110, but not GFP, enhances Wy 14,643-induced (PPARα agonist-induced) expression of genes involved in fatty acid oxidation and increase palmitate oxidation in 3T3-L1 cells. Because the effect of Sp110 on PPARα is expected to require direct interaction between the two proteins, Sp110 is expected to be more effective than Sp110m at producing these changes. If Sp110 and Sp110m are equally effective at inducing fatty acid oxidation, the putative LXXLL interaction domain in Sp110 is deemed non-crucial for this effect. In that event, studies to define alternative interaction sites between PPARα and Sp110 could be carried out.

3T3-L1 cells express relatively low levels of PPARα. In fact, these levels may be too low to detect any effect of Sp110 on genes normally regulated by PPARα. Thus, if there appears to be no enhancement of expression of genes involved in fatty acid oxidation following infection with Ad.Sp110, the studies are performed using an adenovirus vector encoding PPARα. Successful production of PPARα is confirmed using immunoblots and a commercially available anti-PPARα antibody. 3T3-L1 cells will be infected with Ad.GFP, Ad.Sp110, Ad.PPARα, or both Ad.Sp110 and Ad.PPARα. The effect of Ad.PPARα and Ad.Sp110 (together) on the expression of fatty acid oxidation genes and palmitate oxidation rates is compared to the effect of Ad.Sp110, Ad.PPARα, and Ad.GFP alone.

Example 8

Expression of Sp110 in hCASMCs and IL-1-Induced Production of IL-6 and Cyclooxygenase (COX)-2

Inflammatory cytokines such as IL-1 induce expression of IL-6 and COX-2 in smooth muscle cells (SMCs). This expression can be blocked, however, if the SMCs are; treated with PPARα agonists (Staels et al., *J. Clin. Invest.* 103:1489–1498, 1999). Endogenous Sp110 expression in SMCs was enhanced by treatment with inflammatory cytokines. Thus, Sp110 is expected to enhance PPARα-mediated inhibition of the inflammatory response in SMCs.

Forty-eight hours after human coronary artery SMCs (hCASMCs) are infected with Ad.Sp110, they are treated with recombinant human IL-1 and Wy14,643. The amount of IL-6 released by SMCs is measured by radioimmunoassay. To confirm that the effect of Ad.Sp110 on PPARα-mediated inhibition of IL-6 production is not a result of the Ad vector alone, control cells are infected, in parallel, with Ad.GFP at the same MOI as used for Ad.Sp110. Cells are treated with IL-1 and Wy14,643 and IL-6 production are measured as described above.

Because Sp110 also is expected to augment the ability of PPARα to inhibit COX-2 gene expression, SMCs are infected with Ad.Sp110 and subsequently treated with IL-I as described above. The cells are treated with increasing amounts of the PPARα agonist Wy14,643 and the concentration of COX-1 and COX-2 protein will be measured using immunoblot techniques. Parallel experiments are conducted with Ad.GFP as a control.

While the concentration of COX-1 is expected to be unaffected either by expression of Sp110 or by treatment with IL-1 or WY14,643, the concentration of COX-2 is expected to change. A lower concentration of COX-2 at each dose of WY14,643 in Ad.Sp110-infected cells (relative to Ad.GFP-infected cells), would suggest that Sp110 augments the ability of PPARα to inhibit COX-2 expression in SMCs in response to IL-I.

Example 9

Inhibiting PPARα-Sp110 Interaction in Cytokine-Treated hCASMCs

The biological function of Sp110 can be assessed in numerous ways, including studies in which it is overexpressed (as can be done to investigate its role in PPARα-mediated signal transduction) and studies in which oligopeptides are used as inhibitors (as can be done to inhibit the ligand-dependent interaction between PPARα and Sp110).

Two complementary oligonucleotides encoding a peptide that spans seven amino acids on either side of the LXXLL domain of Sp110 are synthesized and ligated, in frame, to GAL4 in a eukaryotic expression plasmid (pGAL-LXXL). To demonstrate that the GAL4-oligopeptide fusion protein acts an, inhibitor, this expression plasmid are co-transfected into COS cells with plasmids encoding PPARα, Sp110, and a reporter gene construct in which the reporter is driven by PPRE. As a control, cells are transfected in parallel with a plasmid encoding pGAL alone. The use of GAL4 as a fusion partner facilitates nuclear localization of the oligopeptide. In addition, successful production of the GAL4-oligopeptide fusion protein in transfection assays is confirmed by immunoblotting with anti-GAL4 antibodies. Expression of the GAL4-oligopeptide in COS cells is expected to block agonist-specific, Sp110-mediated, activation of PPARα.

To examine the effect of inhibiting the interaction between PPARα and Sp110 in hCASMCs, an adenovirus vector encoding GAL4-LXXLL and a control virus encoding GAL4 fused to the same amino acid residues in random rearrangement are prepared. hCASMCs are treated with IL-1 and subsequently infected with either Ad.GAL4-

LXXLL or the control adenovirus vector. The production of IL-6 and the induction of COX-2 are assayed as described above.

Treatment of hCASMCs with cytokines induces expression of Sp110. Overexpression of an oligopeptide corresponding to the LXXLL domain in Sp110 would be expected to block Sp110 coactivation of PPARα-mediated gene expression. Thus, the oligopeptide is expected to enhance the cytokine-mediated induction of IL-6 and COX-2.

Example 10

Sp110 Interaction with PPARα

Mutations in the putative nuclear hormone receptor interaction domain of Sp110 inhibit the ability of Sp110 to enhance PPARα-mediated transcriptional activity. These results suggest that the LXXLL domain in Sp110 interacts with PPARα. It is possible, however, that other portions of Sp110 also mediate its interaction with PPARα. Mammalian two-hybrid assays are used to identify the portions of Sp110 and PPARα that mediate functional interaction between these two proteins.

To identify the portion(s) of Sp110 that mediate interaction with PPARα, DNA molecules encoding portions of Sp110 (the Sp100-like region, putative activation domain, SAND domain, LXXLL domain, PHD, and bromodomain, individually and in combination) are ligated into the eukaryotic expression vector pVP16 in-frame with the HSV VP16 activation domain. Each of the resulting plasmids are co-transfected into COS cells with a second plasmid encoding PPARα and a reporter gene containing a PPRE. Successful, production of each fragment of Sp110 is confirmed using immunoblots and an antibody directed against VP16. The ability of each VP16-Sp110 fusion protein to enhance reporter gene expression in the presence of PPARα and agonist provides evidence for a functional interaction between a given Sp110 portion and PPARα. Control experiments are conducted to rule out the possibility that VP16-Sp110 fusion proteins activate the reporter gene in the absence of PPARα. In addition, the inability of PPARα and VP16-Sp110 fusion proteins to activate reporter gene expression from a plasmid that lacks the PPRE will be confirmed.

To identify portions of PPARα that mediate interaction with Sp110, DNA molecules encoding portions of PPARα will be ligated into a eukaryotic expression plasmid in-frame with GAL4. The plasmids will be co-transfected with a plasmid encoding Sp110 fused to VP16 and a reporter gene with an upstream GAL4 response element. Gene expression mediated by GAL4-PPARα-fragment and Sp110 will be compared to that mediated by the same GAL4-PPARα-fragment and control plasmid. The ability of VP16-Sp110 to enhance GAL4-PPARα-fragment-induced reporter gene expression will be evidence of an interaction between Sp110 and a PPARα fragment.

These studies will identify the portions of Sp110 and PPARα that mediate functional interaction between the two proteins. Among others, the interaction domains should include the LXXLL domain of Sp110 and the ligand-binding "activation function 2" (AF2) portion of PPARα.

Example 11

Sp110 Direct Interaction with PPARα

Sp110 is predicted to interact directly with PPARα. A GST-Sp110 fusion protein is prepared and tested in vitro for interaction with $^{35}$S-radiolabeled PPARA. DNA encoding Sp110 is ligated in-frame with DNA encoding glutathione-S-transferase (GST) in the prokaryotic expression plasmid pGEX so as to encode a GST-Sp110 fusion protein. The recombinant fusion protein is expressed in E. coli, affinity-purified, and immobilized on Sepharose beads. DNA encoding PPARα are used to prepare $^{35}$S-radiolabeled protein by in vitro transcription and translation and will be incubated with Sepharose-GST-Sp110 (or Sepharose-GST alone) in the presence and absence of PPARα agonist. Bound and radiolabeled PPARα is eluted from Sepharose-GST-Sp110 (or Sepharose-GST) by boiling in SDS/PAGE sample buffer, and the eluant will be fractionated by SDS/PAGE.

Retention of PPARα on Sepharose-GST-Sp110, but not on control Sepharose-GST, provides evidence for a direct interaction between PPARα and Sp110. In addition, if PPARα is retained on Sepharose-GST-Sp110 in the presence, but not in the absence, of PPARα agonist then the direct interaction between PPARα and Sp110 requires the presence of nuclear hormone receptor agonist.

Example 12

Sp110 Interaction with CBP

A mammalian two-hybrid assay was used to demonstrate a functional interaction between the PHD/bromodomain of Sp110 and amino acids 271–720 of CBP. Sp110 may also interact directly with CBP. To determine whether or not it does, a GST-CBP (271–720) fusion protein will be prepared (as described above for Sp110) and exposed to $^{35}$S-radiolabeled Sp110. An $^{35}$S-radiolabeled nuclear body component, PML, can serve as a positive control for interaction with CBP, as PML interacts with CBP in this portion of the protein (Doucas et al., Proc. Natl. Acad. Sci. USA, 96:2627–2632, 1999). If CBP interacts directly with Sp110, then a Sepharose-GST-CBP (271–720) fusion protein, but not Sepharose-GST alone, would be expected to retain radiolabeled Sp110.

CBP has been described as a "platform" protein because it interacts with many other proteins. Among the proteins that interact with CBP at amino acid residues 271–720 are: RXR, STAT2, CREB, JUN, MYYB, ELK1, SREBP, and SAP1A (Giles et al., Trends Genetics, 14:178–183, 1998). Instead of a direct interaction between Sp110 and CBP, at least one other protein may mediate the functional interaction between these two proteins. If a direct interaction between Sp110 and CBP cannot be demonstrated using GST pulldown experiments, then the mammalian two-hybrid system will be used to further delineate the site in CBP that mediates functional interaction with Sp110. Two approaches can then be taken to identify the protein(s) that link CBP and Sp110. A candidate gene approach will involve obtaining cDNAs encoding proteins that are known to interact with the identified portion of CBP. Proteins encoded by these cDNAs will be tested for interaction with Sp110 using a combination of GST pull-down and mammalian two-hybrid assays. If none of the candidate genes interacts with Sp110, then the yeast two-hybrid system will be used to identify cDNAs encoding proteins that link CBP and Sp110. A DNA fragment encoding the PHD/bromodomain of Sp110, and a DNA fragment encoding the portion of CBP that mediates functional interaction with Sp110, will each be used to screen a human leukocyte cDNA library. Complementary DNAs encoding interacting proteins will be divided into groups that interact with Sp110, CBP, or both. Verification of "true" protein-protein interactions are then performed, as described below.

Example 13

Sp110 SAND Domain and Transcriptional Activation

Sp110 appears to enhance expression of nuclear hormone responsive genes by binding to a nucleotide sequence adjacent to the nuclear hormone response element and directly or indirectly enhancing gene expression. The sand domain of Sp110 may mediate DNA binding. By interacting directly with DNA, Sp110 may enhance gene expression independent of the LXXLL motif. A GAL4-Sp110 fusion protein is capable of activating expression of a reporter gene driven by the GAL4 response element, and neither the N-terminal, which contains the Sp100-like domain, nor the C-terminal, which contains the LXXLL/PHD/bromodomain) of Sp110 are required to mediate enhanced expression of the reporter gene. The middle portion of Sp110 contains a SAND domain, an amino acid sequence motif that has been observed in several proteins that regulate gene transcription.

To identify and characterize cDNAs encoding proteins that interact with Sp110's activation domain, a DNA fragment encoding that domain will be used as "bait" in the yeast two-hybrid assay. The DNA fragment are ligated into plasmid pGBKT7 (Clontech) and transferred into yeast with a leukocyte cDNA library prepared in pGADT7. The transformed yeast will be screened for the ability to grow on His⁻ medium and colonies that grow on this medium will be tested for α-galactosidase (α-gal) activity. Complementary DNAs are recovered from positive yeast clones and re-tested for interaction with bait by a second round of transformation in yeast. If numerous positive clones are obtained, they will be sorted into groups on the basis of size and restriction sites, and representative clones will be tested for interaction with an unrelated bait fusion protein. Clones encoding proteins that specifically interact with the Sp110 activation domain, but not the unrelated protein, will be sequenced and further characterized In vitro co-immunoprecipitation, in vivo co-immunoprecipitation and mammalian two-hybrid assays will be used to confirm functional interactions between Sp110 and proteins produced by cDNAs identified using yeast two-hybrid. These studies identify cDNAs encoding proteins that interact with the activation domain of Sp110. The identity of these proteins will provide additional information regarding the mechanism by which Sp110 functions as a nuclear hormone receptor co-activator.

In an alternative approach, proteins that interact with the activation domain are identified by purifying interacting proteins from cell extracts using recombinant Sp110 protein linked to Sepharose beads. Purified proteins will be fractionated in polyacrylamide gels, transferred to IMMOBILON™ filters, and subjected to amino acid microsequencing. These techniques have been used previously to purify and identify the predominant autoantigen in patients with autoimmune sensorineural hearing loss (Bloch et al., *Archives of Otolaryngology-Head and Neck Surgery* 121: 1167–1171, 1995).

Example 14

Sp110 in PBC Diagnosis

This study demonstrates that antibodies directed against nuclear body components Sp140 and Sp110 identify a subset of PBC patients with a variant form, e.g., a relatively mild form, of PBC. Serum from a well-defined cohort of 370 PBC patients are tested by immunoblot for antibodies directed against Sp110 and Sp140.

Adenovirus vectors containing cDNAs encoding Sp140, Sp110, and Sp100 produce high levels of protein in human 293 cells. Aliquots of cell lysates sufficient to screen 5,000 sera for each of these antigens are prepared. Cell lysates are boiled in loading buffer, fractionated in an 8% polyacrylamide gel, and transferred to nitrocellulose membranes. A miniblot apparatus is applied to the membrane. This permits screening of 20 sera on each membrane. As a preliminary screen, patient serum is diluted 1:200 in PBS containing 5% nonfat dry milk and incubated for one hour at room temperature with the nitrocellulose. Membranes are washed three times with PBS and incubated with horseradish peroxidase (HRP) conjugated-protein A diluted 1:5000 in PBS. Filters are washed three times in PBS, incubated with chemiluminescence reagent, and then exposed to film. If a serum sample appears to contain antibodies directed against the recombinant protein, then a second immunoblot is performed. This second membrane has two lanes, one containing protein from 293 cells infected with adenovirus encoding the nuclear body protein, and the second containing protein from cells infected with the control adenovirus. The presence of an appropriate size band in the former lane, but not the latter, is taken as confirmation of the presence of autoantibodies directed against the nuclear body component. This second immunoblot excludes false-positive results that may be secondary to human antibodies reacting with 293 cell proteins or adenovirus proteins produced in these cells.

The diagnosis of PBC in the 370-patient cohort is established based on the presence of abnormal liver function tests, AMA (titer≧1:20) and liver biopsy compatible with PBC. The findings on liver biopsy are classified into four stages (portal hepatitis, periportal hepatitis, septal fibrosis and/or bridging necrosis, cirrhosis). The cohort includes 234 women and 36 men. The date of presentation was defined as the first documentation of abnormal liver enzymes. The median age at presentation is 52 years (range 24–81). The median length of follow-up is nine years (range 1–27). Symptoms of PBC in these patients include pruritus, jaundice, portosystemic encephalopathy, bleeding varices, edema and ascites. Endpoints of the study are liver transplantation, death from liver disease and death from other causes.

To demonstrate that antibodies directed against Sp110 and Sp140 identify a subset of patients with a mild form of PBC, serum from these patients are screened for the presence of antibodies using immunoblot as described above. For the purpose of this study, mild disease is defined as liver biopsy at presentation showing stage I or II disease and survival during the course of the study without requiring liver transplantation.

Other Embodiments

A number of embodiments of the invention have been described. Nevertheless, it is understood that various modifications may be made without departing from the spirit and scope of the invention. Other embodiments are within the scope of the claims that follow.

What is claimed is:

1. A substantially pure polypeptide comprising the amino acid sequence of SEQ ID NO:2.

2. The polypeptide of claim 1, wherein the polypeptide consists of the amino acid sequence of SEQ ID NO:2.

3. The polypeptide of claim 1, further comprising a membrane transport moiety.

4. The polypeptide of claim 3, wherein the membrane transport moiety is selected from the group consisting of the internalization peptide sequence derived from Antennapedia and an HIV tat peptide.

5. A substantially pure polypeptide consisting of the amino acid sequence of SEQ ID NO:2 and a membrane transport moiety.

6. The polypeptide of claim 5, wherein the membrane transport moiety is selected from the group consisting of the internalization peptide sequence derived from Antennapedia and an HIV tat peptide.

7. A substantially pure polypeptide comprising the amino acid sequence of SEQ ID NO:2 with one or more, but not more than 20, conservative amino acid substitutions therein.

8. The polypeptide of claim 7, wherein the polypeptide comprises SEQ ID NO:2 with 5, 10, 15 or 20 conservative amino acid substitutions therein.

9. The polypeptide of claim 8, further comprising a membrane transport moiety.

10. The polypeptide of claim 9, wherein the membrane transport moiety is selected from the group consisting of the internalization peptide sequence derived from Antennapedia and an HIV tat peptide.

11. A substantially pure polypeptide comprising an Sp110 Sp100-like domain (amino acids 6–109 of SEQ ID NO:2) and an Sp110 SAND domain (amino acids 454–532 of SEQ ID NO:2), but lacking the sequence of amino acids 110–453 of SEQ ID NO:2.

12. The polypeptide of claim 11, wherein the polypeptide consists of an Sp110 Sp100-like domain (amino acids 6–109 of SEQ ID NO:2) and an Sp110 SAND domain (amino acids 454–532 of SEQ ID NO:2).

13. A substantially pure polypeptide comprising an Sp110 Sp100-like domain (amino acids 6–109 of SEQ ID NO:2) and an Sp110 plant homeobox domain (amino acids 537–577 of SEQ ID NO:2), but lacking the sequence of amino acids 110–453 of SEQ ID NO:2.

14. The polypeptide of claim 13, wherein the polypeptide consists of an Sp110 Sp100-like domain (amino acids 6–109 of SEQ ID NO:2) and an Sp110 plant homeobox domain (amino acids 537–577 of SEQ ID NO:2).

15. A substantially pure polypeptide comprising an Sp110 Sp-100-like domain (amino acids 6–109 of SEQ ID NO:2), an Sp110 SAND domain (amino acids 454–532 of SEQ ID NO:2), an Sp110 plant homeobox domain (amino acids 537–577 of SEQ ID NO:2), and an Sp110 bromodomain (amino acids 606–674 of SEQ ID NO:2), wherein the sequence of amino acids 110 to 453 of SEQ ID NO:2 is not present.

16. A substantially pure polypeptide consisting of an Sp110 Sp-100-like domain (amino acids 6–109 of SEQ ID NO:2), an Sp110 SAND domain (amino acids 454–532 of SEQ ID NO:2), an Sp110 plant homeobox domain (amino acids 537–577 of SEQ ID NO:2), and an Sp110 bromodomain (amino acids 606–674 of SEQ ID NO:2)

* * * * *